US012336793B1

(12) United States Patent
Inan et al.

(10) Patent No.: US 12,336,793 B1
(45) Date of Patent: Jun. 24, 2025

(54) SYSTEMS AND METHODS FOR MEASURING HEMODYNAMIC PARAMETERS WITH WEARABLE CARDIOVASCULAR SENSING

(71) Applicant: Georgia Tech Research Corporation, Atlanta, GA (US)

(72) Inventors: Omer T. Inan, Atlanta, GA (US); Varol Burak Aydemir, Atlanta, GA (US); James Rehg, Atlanta, GA (US); Md Mobashir Hasan Shandhi, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 18/751,868

(22) Filed: Jun. 24, 2024

Related U.S. Application Data

(63) Continuation of application No. 18/200,393, filed on May 22, 2023, now abandoned, which is a
(Continued)

(51) Int. Cl.
*A61B 5/352* (2021.01)
*A61B 5/00* (2006.01)
(Continued)

(52) U.S. Cl.
CPC ........ *A61B 5/02141* (2013.01); *A61B 5/1102* (2013.01); *A61B 5/352* (2021.01); *A61B 5/6801* (2013.01); *A61B 5/7214* (2013.01)

(58) Field of Classification Search
CPC .............. A61B 5/02141; A61B 5/1102; A61B 5/352; A61B 5/6801; A61B 5/7214
See application file for complete search history.

(56) References Cited

U.S. PATENT DOCUMENTS 8,238,718 B2  12/2012  Tran
8,328,718 B2  12/2012  Tran
(Continued)

FOREIGN PATENT DOCUMENTS

WO    2016179425 A1    11/2016
WO    2020037391 A1    2/2020
WO    WO-2022115228 A1 *  6/2022  ............. A61B 5/021

OTHER PUBLICATIONS

Search report from European application No. 21898909.3 dated Sep. 3, 2024.
(Continued)

*Primary Examiner* — Andrey Shostak
(74) *Attorney, Agent, or Firm* — Troutman Pepper Locke LLP; Ryan A. Schneider; Brandon M. Reed

(57) ABSTRACT

Systems and methods for measuring hemodynamic parameters with wearable cardiovascular sensing. An apparatus can include one or more sensors configured to measure an electrocardiogram signal of a user and one or more seismocardiogram (SCG) signals of the user, a memory and a processing system including one or more processors operatively coupled to the memory and the one or more sensors, and configured to receive the electrocardiogram and one or more SCG signals, and generate an assessment of heart health by determining one or more hemodynamic parameters based on the signals. The invention further includes a method for non-invasively monitoring heart health of a user including receiving an electrocardiogram signal from a first sensor of a wearable device, receiving one or more SCG signals from a second sensor of the wearable device, and generating the assessment of the heart health of the user by determining the one or more hemodynamic parameters.

23 Claims, 18 Drawing Sheets

Related U.S. Application Data continuation of application No. PCT/US2021/058429, filed on Nov. 8, 2021.

(60) Provisional application No. 63/117,766, filed on Nov. 24, 2020.

(51) Int. Cl.
  *A61B 5/021* (2006.01)
  *A61B 5/11* (2006.01)

(56) References Cited

U.S. PATENT DOCUMENTS

| | | |
|---|---|---|
| 9,801,607 B2 | 10/2017 | Shusterman |
| 11,064,968 B2 | 7/2021 | Shusterman |
| 11,464,451 B1 * | 10/2022 | Zavanelli ............ A61B 5/6833 |
| 2014/0378849 A1 | 12/2014 | Krimsky |
| 2015/0038856 A1 | 2/2015 | Houlton |
| 2016/0095521 A1 | 4/2016 | Inan |
| 2016/0220152 A1 | 8/2016 | Meriheina |
| 2017/0188973 A1 | 7/2017 | Banet |
| 2017/0238847 A1 | 8/2017 | Inan |
| 2017/0311926 A1 | 11/2017 | Vezina |
| 2018/0103916 A1 | 4/2018 | Tscholl |
| 2018/0160917 A1 | 6/2018 | Liu |
| 2018/0358119 A1 | 12/2018 | Bhushan |
| 2019/0175026 A1 * | 6/2019 | Verzal ............... A61B 5/02405 |
| 2020/0196944 A1 | 6/2020 | Minor |
| 2020/0288985 A1 | 9/2020 | Robinson |
| 2023/0293082 A1 | 9/2023 | Inan |

OTHER PUBLICATIONS

International Search Report and Written Opinion from Application No. PCT/US2021/058429 dated Feb. 2022.

International Search Report and Written Opinion dated Feb. 2, 2022 for International Patent Application No. PCT/US2021/058429. 23 pages.

Supplementary European Search Report for EP Application No. EP21898909 dated Aug. 22, 2024. 8 pages.

* cited by examiner

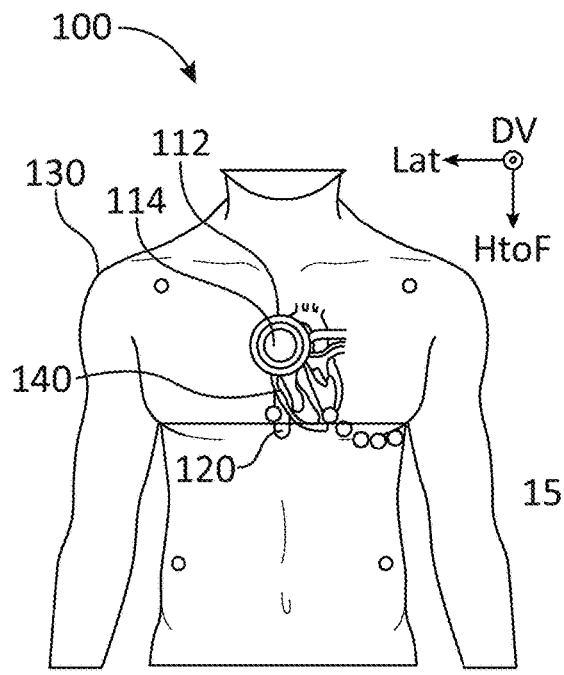
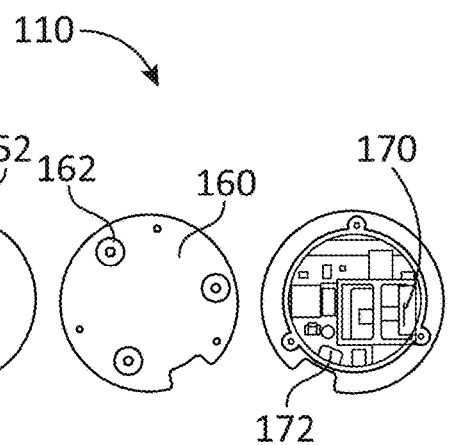
FIG. 1A
FIG. 1B
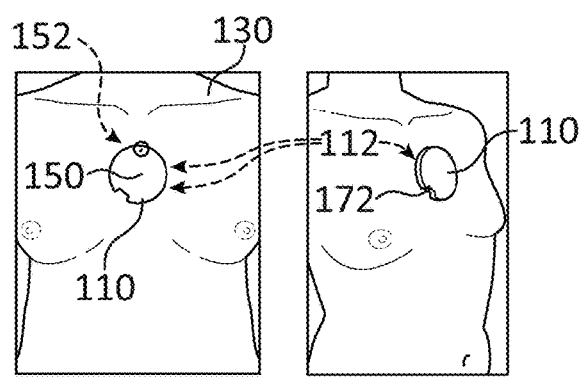
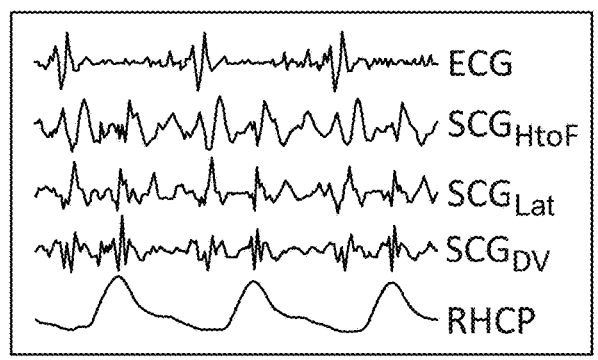
FIG. 1C
FIG. 1D

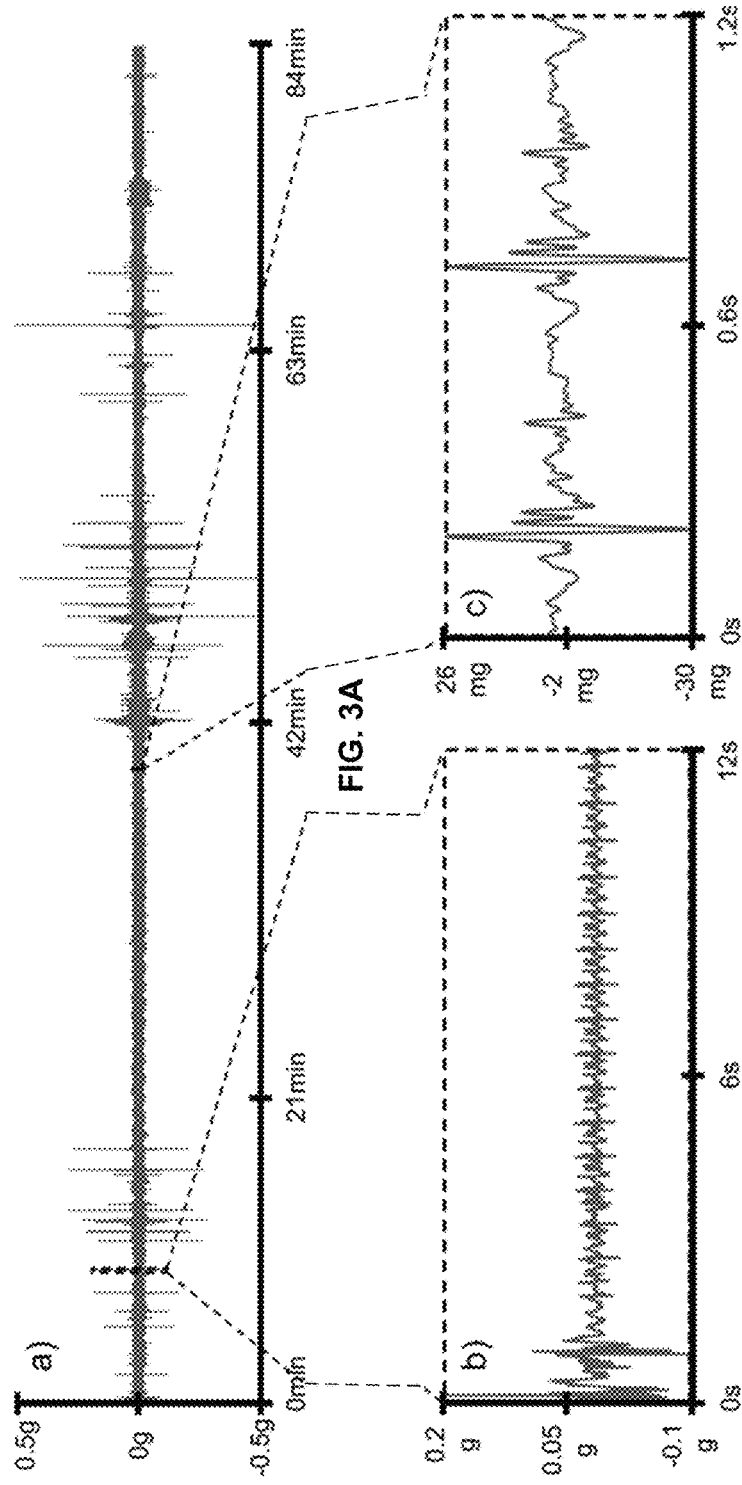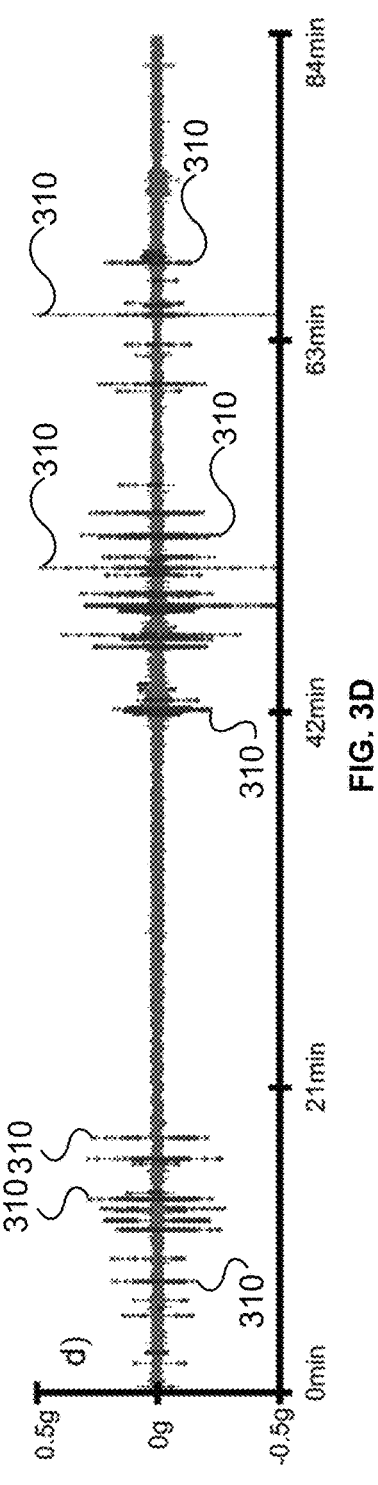

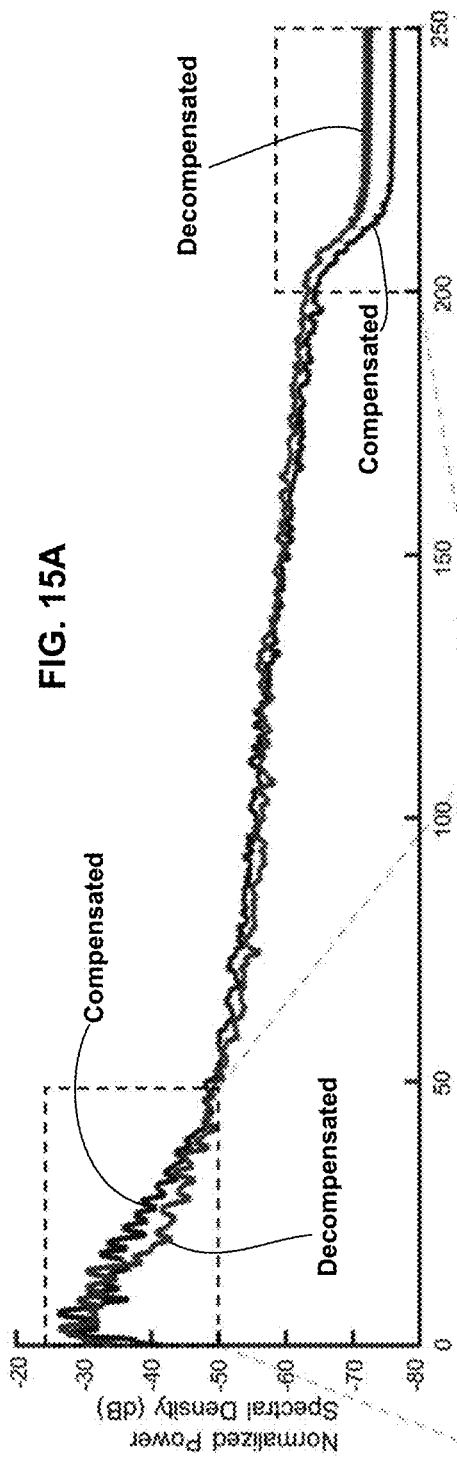
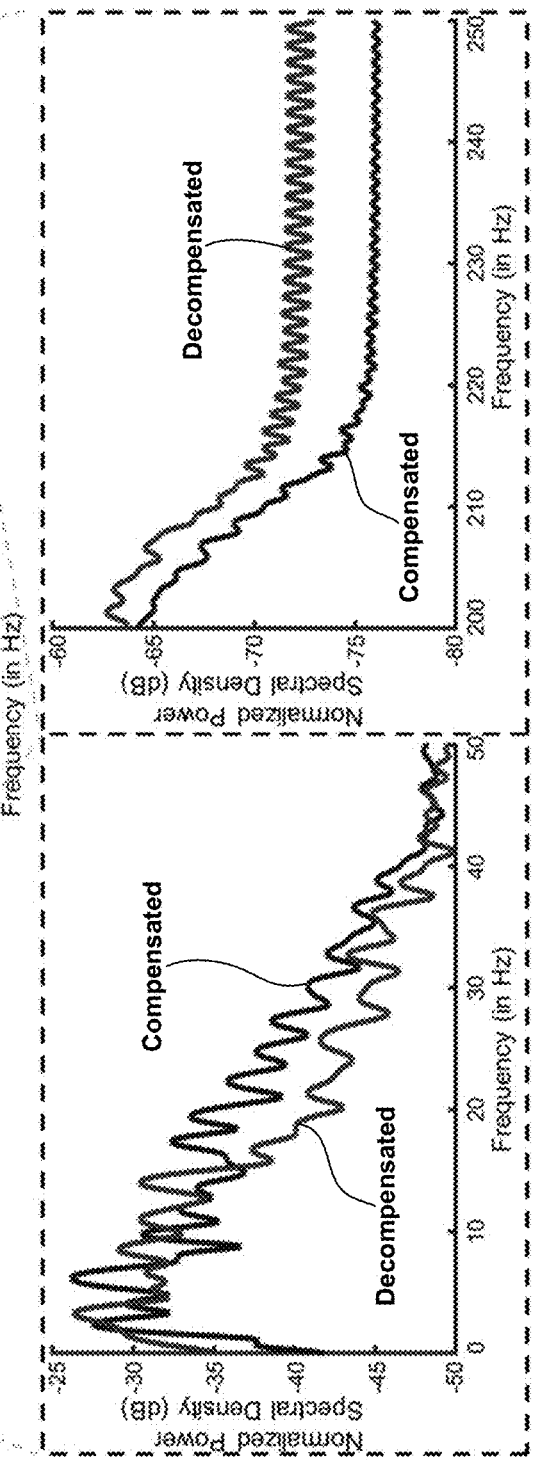
FIG. 15A
FIG. 15B
FIG. 15C

SYSTEMS AND METHODS FOR MEASURING HEMODYNAMIC PARAMETERS WITH WEARABLE CARDIOVASCULAR SENSING

CROSS-REFERENCE TO RELATED APPLICATIONS

This application is a continuation of U.S. patent application Ser. No. 18/200,393, filed May 22, 2023, titled "SYSTEMS AND METHODS FOR MEASURING HEMODYNAMIC C PARAMETERS WITH WEARABLE CARDIOVASCULAR SENSING," now abandoned, which is a continuation of International Patent Application No. PCT/US2021/058429, filed Nov. 8, 2021, titled "SYSTEMS AND METHODS FOR MEASURING HEMODYNAMIC PARAMETERS WITH WEARABLE CARDIOVASCULAR SENSING," which claims priority to U.S. Provisional Patent Application No. 63/117,766, filed Nov. 24, 2020, titled "SYSTEMS AND METHODS FOR MEASURING HEMODYNAMIC PARAMETERS WITH WEARABLE CARDIOVASCULAR SENSING."

STATEMENT REGARDING FEDERALLY SPONSORED RESEARCH OR DEVELOPMENT

This invention was made with government support under 1R01HL130619-A1 awarded by the National Institutes of Health. The government has certain rights in the invention.

SEQUENCE LISTING

Not Applicable

STATEMENT REGARDING PRIOR DISCLOSURES BY THE INVENTOR OR A JOINT INVENTOR

Not Applicable

BACKGROUND OF THE DISCLOSURE

1. Field of the Disclosure

The present disclosure relates generally to health systems and methods and more particularly to a wearable system and method for assessing heart health.

2. Background

Heart failure (HF) is a debilitating disorder contributing each year in the nearly U.S. Pat. No. 300,000 deaths and more than 800,000 hospitalizations. The cost associated with HF exceeds $30 billion per year with an expected increase to $70 billion by 2030. One of the driving factors of the cost and mortality of HF is high rate of rehospitalization of the patients following initial hospitalization. As a result, improved approaches are needed for optimally managing the patients at home to reduce rehospitalizations and thereby improve HF care while reducing costs.

The clinical strategy that has demonstrated the best outcomes in managing patients with HF at home involves the measurement of pulmonary artery (PA) pressures using an implantable device, and titrating therapies according to the presence of elevated PA pressures (indicating congestion or imminent decompensation). While the approach to detecting hemodynamic congestion with PA pressure is sound and validated in large randomized clinical trials, the cost and complications associated with the surgical procedure render the approach only suitable to a small fraction of patients with HF.

Therefore, what is needed is non-invasive and inexpensive technologies enabling the detection of elevated PA pressures without the need for an implantable device allowing patients with HF to be monitored and therapies to be personalized for effective care and improved outcomes such as reduced number of hospitalizations and better quality of life.

BRIEF SUMMARY OF THE DISCLOSURE

The present disclosure relates to health systems and methods. The disclosed technology includes a system for assessing heart health of a user.

In an exemplary embodiment, the present invention is an apparatus comprising a set of electrodes configured to measure an electrocardiogram signal of a heart of a user, the set of electrodes attachable to a chest of the user, and a wearable device configured to be worn on the chest of the user below a suprasternal notch of the user, the wearable device including, a housing having a first side and a second side, the first side configured to face away from the chest and the second side configured to face toward the chest when the wearable device is attached to the set of electrodes, and a set of connectors disposed on the second side of the housing in spaced relation to one another, each of the set of connectors configured to releasably attach to a different electrode of the set of electrodes, an accelerometer disposed within an interior of the housing between the first side and the second side, the accelerometer configured to measure a set of seismocardiogram signals of the user, each seismocardiogram signal of the set of seismocardiogram signals associated with a different axis of a set of axes, and electronics operatively coupled to the set of electrodes and the accelerometer, the electronics including a processor and a memory, the processor configured to execute instructions stored in the memory to, receive the electrocardiogram signal and the set of seismocardiogram signals of the user, segment the set of seismocardiogram signals based on the electrocardiogram signal to construct seismocardiogram beat arrays for the set of axes, each seismocardiogram beat array including a plurality of seismocardiogram signal segments associated with a plurality of beats, remove, from the seismocardiogram beat arrays, motion-contaminated beats by comparing seismocardiogram signal segments of consecutive beats of the plurality of beats with one another to identify one or more seismocardiogram signal segments including motion artifacts, extract, using a machine learning algorithm, features from the seismocardiogram beat arrays after the removing of the motion-contaminated beats, and determine one or more hemodynamic parameters associated with filling characteristics of the heart using the extracted features.

In any of the embodiments disclosed herein, the processor can be further configured to execute instructions stored in the memory to determine one or more hemodynamic parameters associated with at least one of pulmonary artery pressure or pulmonary capillary wedge pressure of the heart using the extracted features.

In any of the embodiments disclosed herein, the set of axes can include a lateral axis, a head-to-foot axis, and a dorso-ventral axis.

In any of the embodiments disclosed herein, the processor can be further configured to execute instructions stored in the memory to generate an assessment of heart health of the user based on the one or more hemodynamic parameters, wherein the heart health of the user is associated with heart failure.

In any of the embodiments disclosed herein, the processor can be further configured to execute instructions stored in the memory to detect R-peaks in the electrocardiogram signal, and the processor is configured to segment the set of seismocardiogram signals based on the R-peaks.

In any of the embodiments disclosed herein, the detecting the R-peaks in the electrocardiogram signal can include implementing at least one of Pan Tompkins or a Phasor Transform to process the electrocardiogram signal to detect the R-peaks.

In any of the embodiments disclosed herein, the processor can be further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

In any of the embodiments disclosed herein, the one or more hemodynamic parameters can include a filling pressure of the user or a change in the filling pressure of the user.

In any of the embodiments disclosed herein, the processor can be further configured to execute instructions stored in the memory to compute an ensemble average of the seismocardiogram beat arrays after the removing of the motion-contaminated beats, wherein the processor is configured to extract the features from the seismocardiogram beat arrays from the ensemble average.

In an exemplary embodiment, the present invention is an apparatus comprising a set of electrodes configured to measure an electrocardiogram signal of a heart of a user, the set of electrodes attachable to a chest of the user, and a wearable device configured to be worn on the chest of the user below a suprasternal notch of the user, the wearable device including, a housing having a first side and a second side, the first side configured to face away from the chest and the second side configured to face toward the chest when the wearable device is attached to the set of electrodes, and a set of connectors disposed on the second side of the housing in spaced relation to one another, each of the set of connectors configured to releasably attach to a different electrode of the set of electrodes, an accelerometer disposed within an interior of the housing between the first side and the second side, the accelerometer configured to measure a set of seismocardiogram signals of the user, each seismocardiogram signal of the set of seismocardiogram signals associated with a different axis of a set of axes, and electronics operatively coupled to the set of electrodes and the accelerometer, the electronics including a processor and a memory, the processor configured to execute instructions stored in the memory to, receive the electrocardiogram signal and the set of seismocardiogram signals of the user, segment the set of seismocardiogram signals based on the electrocardiogram signal to construct seismocardiogram beat arrays for the set of axes, each seismocardiogram beat array including a plurality of seismocardiogram signal segments associated with a plurality of beats, remove, from the seismocardiogram beat arrays, motion-contaminated beats using a motion artifact detection algorithm, extract, using a machine learning algorithm, features from the seismocardiogram beat arrays after the removing of the motion-contaminated beats, and determine one or more hemodynamic parameters associated with filling characteristics of the heart using the extracted features.

In any of the embodiments disclosed herein, the processor can be further configured to execute instructions stored in the memory to, prior to segmenting the set of seismocardiogram signals, apply one or more cut-off frequencies to the set of seismocardiogram signals to remove out-of-band noise associated with the set of seismocardiogram signals.

In any of the embodiments disclosed herein, the set of axes can include a lateral axis, a head-to-foot axis, or a dorso-ventral axis.

In any of the embodiments disclosed herein, the processor can be further configured to execute instructions stored in the memory to detect R-peaks in the electrocardiogram signal, and the processor is configured to segment the set of seismocardiogram signals based on the R-peaks.

In any of the embodiments disclosed herein, the detecting the R-peaks in the electrocardiogram signal can include implementing at least one of Pan Tompkins or a Phasor Transform to process the electrocardiogram signal to detect the R-peaks.

In any of the embodiments disclosed herein, the processor can be further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

In any of the embodiments disclosed herein, the one or more hemodynamic parameters can include a filling pressure of the user or a change in the filling pressure of the user.

In any of the embodiments disclosed herein, the processor can be further configured to execute instructions stored in the memory to compute an ensemble average of the seismocardiogram beat arrays after the removing of the motion-contaminated beats, wherein the processor is configured to extract the features from the seismocardiogram beat arrays from the ensemble average.

In an exemplary embodiment, the present invention is an apparatus comprising aa set of electrodes configured to measure an electrocardiogram signal of a heart of a user, the set of electrodes attachable to a chest of the user, and a wearable device configured to be worn on the chest of the user below a suprasternal notch of the user, the wearable device including, a housing having a first side and a second side, the first side configured to face away from the chest and the second side configured to face toward the chest when the wearable device is attached to the set of electrodes, and a set of connectors disposed on the second side of the housing in spaced relation to one another, each of the set of connectors configured to releasably attach to a different electrode of the set of electrodes, an accelerometer disposed within an interior of the housing between the first side and the second side, the accelerometer configured to measure a set of seismocardiogram signals of the user, each seismocardiogram signal of the set of seismocardiogram signals associated with a different axis of a set of axes, and electronics operatively coupled to the electrodes and the accelerometer, the electronics including a processor and a memory, the processor configured to execute instructions stored in the memory to, receive the electrocardiogram signal and the set of seismocardiogram signals of the user, segment the set of seismocardiogram signals based on the electrocardiogram signal to construct seismocardiogram beat arrays for the set of axes, each seismocardiogram beat array including a plurality of seismocardiogram signal segments associated with a plurality of beats, remove, from the seismocardiogram beat arrays, motion-contaminated beats by comparing the seismocardiogram signal segments of consecutive beats of the plurality of beats with one another to identify one or more seismocardiogram signal segments including motion artifacts, and determine one or more hemodynamic parameters associated with filling characteristics of the heart based on the seismocardiogram beat arrays after removing the motion-contaminated beats.

In any of the embodiments disclosed herein, the processor can be further configured to execute instructions stored in the memory to determine one or more hemodynamic parameters associated with at least one of pulmonary artery pressure or pulmonary capillary wedge pressure of the heart based on the seismocardiogram beat arrays after removing the motion-contaminated beats.

In any of the embodiments disclosed herein, the set of axes can include a lateral axis, a head-to-foot axis, and a dorso-ventral axis.

In any of the embodiments disclosed herein, the processor can be further configured to execute instructions stored in the memory to generate an assessment of heart health of the user based on the one or more hemodynamic parameters, wherein the heart health of the user is associated with heart failure.

In any of the embodiments disclosed herein, the processor can be further configured to execute instructions stored in the memory to detect R-peaks in the electrocardiogram signal, and the processor is configured to segment the set of seismocardiogram signals based on the R-peaks.

In any of the embodiments disclosed herein, the detecting the R-peaks in the electrocardiogram signal can include implementing at least one of Pan Tompkins or a Phasor Transform to process the electrocardiogram signal to detect the R-peaks.

In any of the embodiments disclosed herein, the processor can be further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

In any of the embodiments disclosed herein, the one or more hemodynamic parameters can include a filling pressure of the user or a change in the filling pressure of the user.

In any of the embodiments disclosed herein, the processor can be further configured to execute instructions stored in the memory to compute an ensemble average of the seismocardiogram beat arrays after the removing of the motion-contaminated beats, wherein the processor is configured to extract features from the seismocardiogram beat arrays from the ensemble average.

In another exemplary embodiment, the present invention is an apparatus comprising one or more sensors configured to measure an electrocardiogram (ECG) signal of a user and configured to measure one or more seismocardiogram (SCG) signals of the user, a memory, and a processing system comprising one or more processors operatively coupled to the memory and one or more of the sensors, the processing system configured to receive the ECG signal, receive at least one of the SCG signals, and generate an assessment of heart health of the user by determining one or more hemodynamic parameters based on the ECG signal and the received at least one SCG signal.

One or more of the sensors can comprise a first sensor configured to measure the ECG signal of the user and a second sensor configured to measure one or more of the SCG signals of the user.

In any of the embodiments disclosed herein, at least one of the SCG signals can include at least one SCG signal in at least two axes.

In any of the embodiments disclosed herein, at least two of the axes can includes at least two of a lateral (Lat) axis, a head-to-foot (HtoF) axis, or a dorso-ventral (DV) axis.

In any of the embodiments disclosed herein, the processing system can be further configured to, prior to generating the assessment of heart health, generate a combined SCG signal using the SCG signals in at least two of the axes, the processing system being further configured to determine at least one of the hemodynamic parameters based on the combined SCG signal.

In any of the embodiments disclosed herein, the processing system can be further configured to determine at least one of the hemodynamic parameters based on features extracted from at least one of the SCG signals during at least a diastolic portion of a heartbeat.

In any of the embodiments disclosed herein, the processing system can be further configured to generate the assessment of the heart health by processing, using a classification model, the ECG signal and at least one of the SCG signals to obtain a classification of a clinical status of heart failure (HF) in the user.

In any of the embodiments disclosed herein, at least one of the hemodynamic parameters can include a filling pressure of the user or a change in the filling pressure of the user.

In any of the embodiments disclosed herein, at least one of the hemodynamic parameters can include a pulmonary artery (PA) pressure of the user or a change in the PA pressure of the user.

In any of the embodiments disclosed herein, at least one of the hemodynamic parameters can include a pulmonary capillary wedge pressure (PCWP) of the user or a change in PCWP of the user.

In any of the embodiments disclosed herein, the processing system can be further configured to, prior to generating the assessment of heart health, determine a baseline value of at least one of the hemodynamic parameters for the user, the processing system being further configured to generate the assessment of heart health based on the baseline value.

In any of the embodiments disclosed herein, the processing system can be further configured to determine the baseline value using a population-level regression algorithm.

In any of the embodiments disclosed herein, the processing system can be further configured to determine the baseline value using data collected of the user during a right heart catheterization (RHC) procedure or a clinical exam.

In any of the embodiments disclosed herein, the first sensor and the second sensor can be contained in a wearable housing configured to be worn on a chest of the user below the suprasternal notch.

In any of the embodiments disclosed herein, the first sensor can include at least one electrode configured to be placed against a skin of the user, and the second sensor can include an accelerometer.

In any of the embodiments disclosed herein, the apparatus can further comprise a third sensor configured to measure an environmental parameter, the processing system being further configured to determine at least one of the hemodynamic parameters based on the environmental parameter.

In any of the embodiments disclosed herein, the apparatus can further comprise a third sensor configured to measure a photoplethysmography signal of the user, the processing system being further configured to determine at least one of the hemodynamic parameters based on the photoplethysmography signal.

In any of the embodiments disclosed herein, the apparatus can further comprise a third sensor configured to measure a gyrocardiogram signal of the user. The processing system being further configured to determine at least one of the hemodynamic parameters based on the gyrocardiogram signal.

In another exemplary embodiment, the present invention is an apparatus comprising a housing configured to be worn on a chest of a user below the suprasternal notch, electrodes disposed on the housing and configured to contact a skin of the user and to measure an ECG signal of the user, a sensor disposed in the housing and configured to measure SCG signals of the user in at least two axes, and a controller disposed in the housing, the controller configured to receive the ECG signal from the electrodes, receive the SCG signals from the sensor, determine a baseline value for the user, and generate an assessment of heart health by determining one or more hemodynamic parameters based on the ECG signal, the SCG signals, and the baseline value.

In any of the embodiments disclosed herein, the apparatus can further comprise a sensor disposed in the housing and configured to measure an environmental parameter, the controller being further configured to determine at least one of the hemodynamic parameters based on the environmental parameter.

In any of the embodiments disclosed herein, the environmental parameter can include at least one of a temperature, a humidity, or an altitude.

In any of the embodiments disclosed herein, the apparatus can further comprise a sensor disposed in the housing and configured to measure a photoplethysmography signal of the user, the controller being further configured to determine at least one of the hemodynamic parameters based on the photoplethysmography signal.

In any of the embodiments disclosed herein, the apparatus can further comprise a sensor disposed in the housing and configured to measure a gyrocardiogram signal of the user, the controller being further configured to determine at least one of the hemodynamic parameters based on the gyrocardiogram signal.

In any of the embodiments disclosed herein, the sensor can be configured to measure the SCG signals in three axes.

In any of the embodiments disclosed herein, at least one of the hemodynamic parameters can include a filling pressure of the user or a change in the filling pressure of the user.

In any of the embodiments disclosed herein, at least one of the hemodynamic parameters can include a PA pressure of the user or a change in the PA pressure of the user.

In any of the embodiments disclosed herein, at least one of the hemodynamic parameters can include a PCWP of the user or a change in PCWP of the user.

In any of the embodiments disclosed herein, the controller can be further configured to determine the baseline value by determining, using a population-level regression algorithm, at least one of a baseline filling pressure, a baseline PA pressure, or a baseline PCWP for the user.

In any of the embodiments disclosed herein, the controller can be further configured to generate the assessment of the heart health by processing, using a classification model, the ECG signal and the SCG signals to obtain a classification of a clinical status of HF in the user.

In another exemplary embodiment, the present invention is a method for non-invasively monitoring heart health of a user, the method comprising receiving an ECG signal from a first sensor of a wearable device, the wearable device being disposed on a chest of a user below the suprasternal notch, receiving one or more SCG signals from a second sensor of the wearable device, and generating an assessment of the heart health of the user by determining one or more hemodynamic parameters based on the ECG signal and at least one of the SCG signals.

In any of the embodiments disclosed herein, at least one of the hemodynamic parameters can include a filling pressure of the user, a PA pressure of the user, or a PCWP of the user.

In any of the embodiments disclosed herein, the method can further comprise, prior to generating the assessment of the heart health, determining a baseline value of at least one of the hemodynamic parameters for the user.

In another exemplary embodiment, the present invention is a system for assessing heart health including a first sensor, a second sensor, a processor, and a memory. The first sensor can be configured to measure at least one electrical characteristic of a heart of the user. The second sensor can be configured to measure cardiogenic vibrations of the user. The memory can include instructions that, when executed by the processor, cause the processor to generate an assessment of heart health of the user comprising data indicative of filling characteristics of the heart based, at least in part, on measurements from the first sensor and the second sensor.

In any of the embodiments disclosed herein, the first sensor can be configured to measure an ECG signal of the user.

In any of the embodiments disclosed herein, the second sensor can be configured to measure a SCG signal of the user.

In any of the embodiments disclosed herein, the memory can include instructions that, when executed by the processor, cause the processor to generate the assessment of heart health of the user comprising data indicative of filling characteristics of the heart based, at least in part, on an Lat axis of the SCG signal of the user.

In any of the embodiments disclosed herein, the memory can include instructions that, when executed by the processor, cause the processor to generate the assessment of heart health of the user comprising data indicative of filling characteristics of the heart based, at least in part, on a HtoF axis of the SCG signal of the user.

In any of the embodiments disclosed herein, the memory can include instructions that, when executed by the processor, cause the processor to generate the assessment of heart health of the user comprising data indicative of filling characteristics of the heart based, at least in part, on a DV axis of the SCG signal of the user.

In any of the embodiments disclosed herein, the memory can include instructions that, when executed by the processor, cause the processor to generate the assessment of heart health of the user comprising data indicative of filling characteristics of the heart based, at least in part, on the SCG signal of the user during a diastolic portion of a heartbeat.

In any of the embodiments disclosed herein, the assessment of heart health can include data indicative of a classification of a clinical status of HF in the user.

In any of the embodiments disclosed herein, the assessment of heart health can include data indicative of an indication of a change in hemodynamics of the user.

In any of the embodiments disclosed herein, the assessment of heart health can include data indicative of an indication of a change in filling pressure of the user.

In any of the embodiments disclosed herein, the assessment of heart health can include data indicative of an indication of a change in PA pressure of the user.

In any of the embodiments disclosed herein, the assessment of heart health can include data indicative of an indication of a change in PCWP of the user.

In any of the embodiments disclosed herein, the memory can include instructions that, when executed by the processor, cause the processor to perform a calibration step to create a baseline for one or more parameters associated with the heart health of the user.

In any of the embodiments disclosed herein, the baseline can be a baseline filling pressure.

In any of the embodiments disclosed herein, the calibration step can include using a population-level regression model to create the baseline.

In any of the embodiments disclosed herein, the calibration step can include using personalized data of the user to create the baseline.

In any of the embodiments disclosed herein, the personalized data can include data from a right heart catherization.

In any of the embodiments disclosed herein, the personalized data can include data from a clinical exam.

In any of the embodiments disclosed herein, the first sensor can include a first wearable sensor for placement proximate the heart. The second sensor can include a second wearable sensor for placement proximate the heart.

In any of the embodiments disclosed herein, the system for assessing heart health can include a third sensor.

In any of the embodiments disclosed herein, the third sensor can be configured to measure environmental parameters.

In any of the embodiments disclosed herein, the third sensor can be configured to measure a photoplethysmography signal of the user.

In any of the embodiments disclosed herein, the second sensor can be configured to measure a gyrocardiogram signal of the user.

In any of the embodiments disclosed herein, the system for assessing heart health can include an output indicative of the heart health of the user.

In any of the embodiments disclosed herein, the system for assessing heart health can include a wireless communicator. The wireless communicator can be configured to wirelessly communicate the assessment of heart health of the user to a remote device.

In any of the embodiments disclosed herein, the system for assessing heart health can be a wearable by the user.

The disclosed technology includes a wearable system for assessing heart health of a user. The wearable system for assessing heart health can include a first sensor, a second sensor, and a controller. The first sensor can be configured to measure at least one electrical characteristic of a heart of the user. The second sensor can be configured to measure cardiogenic vibrations of the user. The controller can be configured to perform a calibration step to create a baseline of one or more parameters associated with a heart health of the user. The controller can be configured to generate an assessment of the heart health of the user comprising data indicative of filling characteristics of the heart based, at least in part, on the baseline and measurements from the first sensor and the second sensor.

In any of the embodiments disclosed herein, the first sensor can be configured to measure an ECG signal of the user.

In any of the embodiments disclosed herein, the second sensor can be configured to measure a SCG signal of the user.

In any of the embodiments disclosed herein, the assessment of heart health of the user comprising data indicative of filling characteristics of the heart can be based, at least in part, on an Lat axis of the SCG signal of the user.

In any of the embodiments disclosed herein, the assessment of heart health of the user comprising data indicative of filling characteristics of the heart can be based, at least in part, on a HtoF axis of the SCG signal of the user.

In any of the embodiments disclosed herein, the assessment of heart health of the user comprising data indicative of filling characteristics of the heart can be based, at least in part, on a DV axis of the SCG signal of the user.

In any of the embodiments disclosed herein, the assessment of heart health of the user comprising data indicative of filling characteristics of the heart can be based, at least in part, on the SCG signal of the user during a diastolic portion of a heartbeat.

In any of the embodiments disclosed herein, the assessment of heart health can include data indicative of a classification of a clinical status of HF in the user.

In any of the embodiments disclosed herein, the assessment of heart health can include data indicative of an indication of a change in hemodynamics of the user.

In any of the embodiments disclosed herein, the assessment of heart health can include data indicative of an indication of a change in filling pressure of the user.

In any of the embodiments disclosed herein, the assessment of heart health can include data indicative of an indication of a change in PA pressure of the user.

In any of the embodiments disclosed herein, the assessment of heart health can include data indicative of an indication of a change in PCWP of the user.

In any of the embodiments disclosed herein, the baseline can be a baseline filling pressure.

In any of the embodiments disclosed herein, the calibration step can include using a population-level regression model to create the baseline.

In any of the embodiments disclosed herein, the calibration step can include using personalized data of the user to create the baseline.

In any of the embodiments disclosed herein, the personalized data can include data from a right heart catherization.

In any of the embodiments disclosed herein, the personalized data can include data comprises data from a clinical exam.

In any of the embodiments disclosed herein, the first sensor can include a first wearable sensor for placement proximate the heart. The second sensor can include a second wearable sensor for placement proximate the heart.

In any of the embodiments disclosed herein, the wearable system for assessing heart health can include a third sensor.

In any of the embodiments disclosed herein, the third sensor can be configured to measure environmental parameters.

In any of the embodiments disclosed herein, the third sensor can be configured to measure a photoplethysmography signal of the user.

In any of the embodiments disclosed herein, the second sensor can be configured to measure a gyrocardiogram signal of the user.

In any of the embodiments disclosed herein, the wearable system for assessing heart health can include an output indicative of the heart health of the user.

In any of the embodiments disclosed herein, the wearable system for assessing heart health can include a wireless communicator. The wireless communicator can be configured to wirelessly communicate the assessment of heart health of the user to a remote device.

In any of the embodiments disclosed herein, the wearable system for assessing heart health can be wearable by the user.

The disclosed technology includes a method for non-invasively monitoring heart health of a user. The method can include receiving, by a wearable device, a first signal indicative of at least one electrical characteristic of a heart of the user. The method can include receiving, by the wearable device, a second signal indicative of cardiogenic vibrations of the user. The method can include generating, based, at least in part, on the first and second signals, an assessment of heart health of the user comprising data indicative of filling characteristics of the heart. The method can include providing an output indicative of the assessment of the heart health of the user.

In any of the embodiments disclosed herein, the first signal can be indicative of an ECG signal of the user.

In any of the embodiments disclosed herein, the second signal can be indicative of a SCG signal of the user.

In any of the embodiments disclosed herein, the assessment of heart health of the user comprising data indicative of filling characteristics of the heart can be based, at least in part, on an Lat axis of the SCG signal of the user.

In any of the embodiments disclosed herein, the assessment of heart health of the user comprising data indicative of filling characteristics of the heart can be based, at least in part, on a HtoF axis of the SCG signal of the user.

In any of the embodiments disclosed herein, the assessment of heart health of the user comprising data indicative of filling characteristics of the heart can be based, at least in part, on a DV axis of the SCG signal of the user.

In any of the embodiments disclosed herein, the assessment of heart health of the user comprising data indicative of filling characteristics of the heart can be based, at least in part, on the SCG signal of the user during a diastolic portion of a heartbeat.

In any of the embodiments disclosed herein, the assessment of heart health can include data indicative of a classification of a clinical status of HF in the user.

In any of the embodiments disclosed herein, the assessment of heart health can include data indicative of an indication of a change in hemodynamics of the user.

In any of the embodiments disclosed herein, the assessment of heart health can include data indicative of an indication of a change in filling pressure of the user.

In any of the embodiments disclosed herein, the assessment of heart health can include data indicative of an indication of a change in PA pressure of the user.

In any of the embodiments disclosed herein, the assessment of heart health can include data indicative of an indication of a change in PCWP of the user.

In any of the embodiments disclosed herein, the method can include calibrating to create a baseline for one or more parameters associated with the heart health of the user.

In any of the embodiments disclosed herein, the baseline can be a baseline filling pressure.

In any of the embodiments disclosed herein, the calibrating can include using a population-level regression model to create the baseline.

In any of the embodiments disclosed herein, the calibrating can include using personalized data of the user to create the baseline.

In any of the embodiments disclosed herein, the personalized data can include data from a right heart catherization.

In any of the embodiments disclosed herein, the personalized data can include data from a clinical exam.

In any of the embodiments disclosed herein, the wearable device can be placed proximate the heart.

In any of the embodiments disclosed herein, the method can include receiving a third signal.

In any of the embodiments disclosed herein, the third signal can be indicative of at least one environmental parameter.

In any of the embodiments disclosed herein, the third signal can be indicative of a photoplethysmography signal of the user.

In any of the embodiments disclosed herein, the second signal can be indicative of a gyrocardiogram signal of the user.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features can also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 1A provides an illustration of an example system for assessing heart health, in accordance with the present disclosure.

FIG. 1B provides photos of an example system for assessing heart health, in accordance with the present disclosure.

FIG. 1C provides photos of an example system for assessing heart health, in accordance with the present disclosure.

FIG. 1D provides example signal data from a system for assessing heart health, in accordance with the present disclosure.

FIG. 3A provides a graph of experimentally measured SCG data, in accordance with the present disclosure.

FIG. 3B provides a graph of experimentally measured SCG data, in accordance with the present disclosure.

FIG. 3C provides a graph of experimentally measured SCG data, in accordance with the present disclosure.

FIG. 3D provides a graph of experimentally measured SCG data, in accordance with the present disclosure.

FIG. 15A provides a plot of power spectral density (PSD) based on an average of each PSD of each individual SCG beat for a decompensated curve from a randomly selected decompensated subject and a compensated curve from a randomly selected compensated subject, in accordance with the present disclosure.

FIG. 15B provides a callout of the lower frequency range (5-40 Hz) of FIG. 15A, in accordance with the present disclosure.

FIG. 15C provides a callout of the higher frequency range (200-250 Hz) of FIG. 15A, in accordance with the present disclosure.

DETAILED DESCRIPTION

Figure 1E:
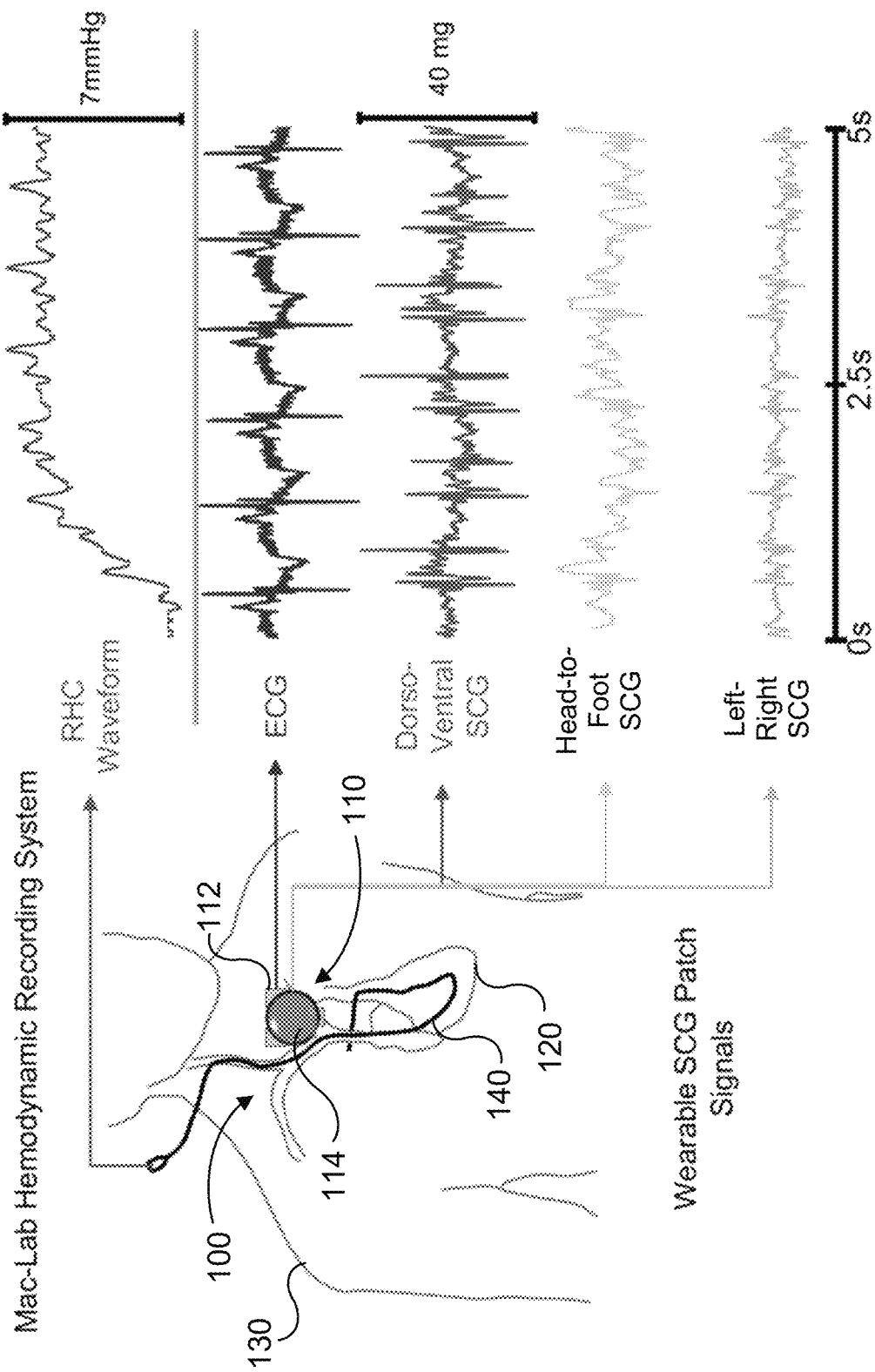
FIG. 1E provides an illustration of an example system for assessing heart health and example signal data, in accordance with the present disclosure.

Throughout this disclosure we describe systems and methods for assessing heart health, such as, a wearable system and method that assesses the health status of a user's heart. For example, an embodiment of the disclosure provides a wearable, minimally obtrusive system to remotely monitor HF patients using wearable seismocardiography (SCG). As such, the system can assess the heart health of a user and inform the user and/or caregiver of the results. For example, the system can estimate internal filling pressures of the heart which can be representative of congestion (preload).

While the disclosed technology is described throughout this disclosure in relation to systems and methods for assessing heart health, those having skill in the art will recognize that the disclosed technology is not so limited and can be applicable to other scenarios and applications. For example, it is contemplated that the disclosed technology can be applicable to any application where quantifying preload is relevant, including hemorrhage monitoring and detection of cardiovascular collapse from hypovolemia.

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Indeed, it is to be understood that other examples are contemplated. Many suitable components that would perform the same or similar functions as components described herein are intended to be embraced within the scope of the disclosed electronic devices and methods. Such other components not described herein may include, but are not limited to, for example, components developed after development of the disclosed technology.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified. Further, it is contemplated that the disclosed methods and processes can include, but do not necessarily include, all steps discussed herein. That is, methods and processes in accordance with the disclosed technology can include some of the disclosed while omitting others.

Throughout the specification and the claims, the following terms take at least the meanings explicitly associated herein, unless otherwise indicated. The term "or" is intended to mean an inclusive "or." Further, the terms "a," "an," and "the" are intended to mean one or more unless specified otherwise or clear from the context to be directed to a singular form. By "comprising," "containing," or "including" it is meant that at least the named element, or method step is present in article or method, but does not exclude the presence of other elements or method steps, even if the other such elements or method steps have the same function as what is named.

As used herein, unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Although the disclosed technology may be described herein with respect to various systems and methods, it is contemplated that embodiments or implementations of the disclosed technology with identical or substantially similar features may alternatively be implemented as methods or systems. For example, any aspects, elements, features, or the like described herein with respect to a method can be equally attributable to a system. As another example, any aspects, elements, features, or the like described herein with respect to a system can be equally attributable to a method.

Reference will now be made in detail to examples of the disclosed technology, examples of which are illustrated in the accompanying drawings and disclosed herein. Wherever convenient, the same reference numbers will be used throughout the drawings to refer to the same or like parts.

Referring now to the drawings, in which like numerals represent like elements, examples of the present disclosure are herein described. As will be described in greater detail, the present disclosure can include a system and method for assessing heart health. To provide a background of the system described in the present disclosure, components of the system for assessing heart health is shown in FIG. 1A and will be discussed first.

To facilitate an understanding of the principles and features of the present disclosure, various examples of the disclosed technology are explained herein. The components, steps, and materials described herein as making up various elements of the disclosed technology are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

As used herein, unless otherwise noted, the term "heart health" refers to the health of the entire heart and cardiovascular system.

As used herein, unless otherwise noted, the term "signal" refers to one or more signals.

As shown in FIGS. 1A and 1E, the disclosed technology includes a system for assessing heart health 100. The system 100 can include a wearable device 110. The wearable device 110 can be a device worn on a person (e.g., a user 130). Alternatively, or in addition, the wearable device 110 can be configured to be positioned proximate a heart 120 of the user 130. For example, as illustrated in FIGS. 1A and 1E, the wearable device 110 can be worn on the chest of a user 130.

The wearable device 110 can include one or more sensors. For example, the wearable device 110 can include a first sensor 112. Alternatively, or in addition, the wearable device 110 can include a second sensor 114.

The first sensor 112 can be configured to measure at least one electrical characteristic of a heart. For example, the first sensor 112 can measure an electrocardiogram (ECG) signal of the user 130. The first sensor 112 can include one or more electrodes that can be placed on the body of the user 130. For example, the one or more electrodes can be stuck to the skin of the user 130. Alternatively, or in addition, the one or more electrodes being stuck to the skin of the user 130 can further affix the wearable device 110 to the user.

The second sensor 114 can be configured to measure cardiogenic vibrations of the user. For example, the second sensor can be configured to measure a seismocardiogram (SCG) signal of the user 130. The second sensor 114 can be configured to measure tri-axial SCG signals. For example, tri-axial SCG signals can include the DV, Lat, and/or HtoF axis. Alternatively, or in addition, the second sensor 114 can be configured to measure a gyrocardiogram signal of the user.

The system 100 can alternatively, or in addition, include a catheter 140. The catheter 140 can be inserted into a user's body to measure hemodynamic parameters. For example, the catheter 140 can be inserted into a user 130 who is undergoing a right heart catheterization (RHC) procedure.

As shown in FIGS. 1B and 1C, the wearable device 110 can include a first side 150 and a second side 160. For example, the wearable device can have an external structure that includes a first side 150 and second side 160. The first side 150 and second side 160 can be connectable and separable structures. The first side 150 and second side 160 can be generally round in shape and connectable to create a generally puck-like shape. Alternatively, or in addition, the wearable device 110 can include electronics 170 for carrying out the various operations of the wearable device 110. For example, the electronics 170 can be located inside the wearable device 110 between the first side 150 and second side 160.

The first side 150 can be configured to face away from the body of a user 130 (e.g., distal the heart 120). The first side 150 can include an alignment marker 152. For example, the alignment marker 152 can be an arrow for indicating a direction that the wearable device 110 should be oriented when worn by a user (e.g., arrow should face towards head of user 130).

The second side 160 can be configured to face the body of a user 130 (e.g., proximal the heart 120). The second side 160 can include connectors 162. The connectors 162 can connect to the first sensor 112. For example, the first sensor 112 can include one or more electrodes that can be stuck on the body of the user 130 and the connectors 162 can connect the second side 160 to the one or more electrodes. In doing so, the wearable device 110 can be affixed to the user by the one or more electrodes of the first sensor 112 being stuck to the user 130 and the other portions of the wearable device 110 (e.g., second sensor 114, first side 150, second side 160, and electronics 170) being connected to the one or more electrodes by the connectors 162. The connectors 162 can be any connector known in the art, including, but not limited to buttons, snap buttons, press buttons, adhesive, hook and loop, and the like, or any combination thereof.

The electronics 170 can include electronic components of the system 100. The electronics 170 can include a processor and a memory. For example, the electronics 170 can include CPU, microprocessor, and the like. The memory can comprise logical instructions that, when executed by the processor, cause the processor to carry out one of more of the functions disclosed herein. Alternatively, or in addition, the memory can include a removeable memory card. For example, a micro secure digital (microSD) card where the collected data (e.g., from the one or more sensors) can be saved. Alternatively, or in addition, the electronics 170 can include a transceiver. For example, the transceiver can receive data from the one or more sensors (e.g., first sensor 112, second sensor 114) and transmit data to a remote device. Alternatively, or in addition, the electronics can include a plug 172. The plug 172 can be configured to provide power to the wearable device 110. For example, the plug 172 can be connected to a power source to directly power the wearable device 110 and/or charge a battery of the wearable device 110. Alternatively, or in addition, the plug 172 can be configured to connect (e.g., send and receive data) with an external device. For example, the plug can allow for the wearable device to be connected to an external computer, tablet, mobile phone, other processor, and the like, to send and receive data. The plug 172 can be a USB connector. The electronics 170 can include a power source. For example, the power source can be a battery for powering the components of the wearable device (e.g., first sensor 112, second sensor 114, processor, transceiver). Alternatively, or in addition, the electronics can include one or more additional sensors (in addition to the first and second sensors 112, 114). For example, the electronics can include a third sensor.

The third sensor can be configured to measure environmental parameters. For example, the third sensor can be configured to measure one or more of temperature, humidity, altitude, and the like, or any combination thereof. Alternatively, or in addition, the third sensor can be configured to measure a photoplethysmography signal of the user.

Figure 11:
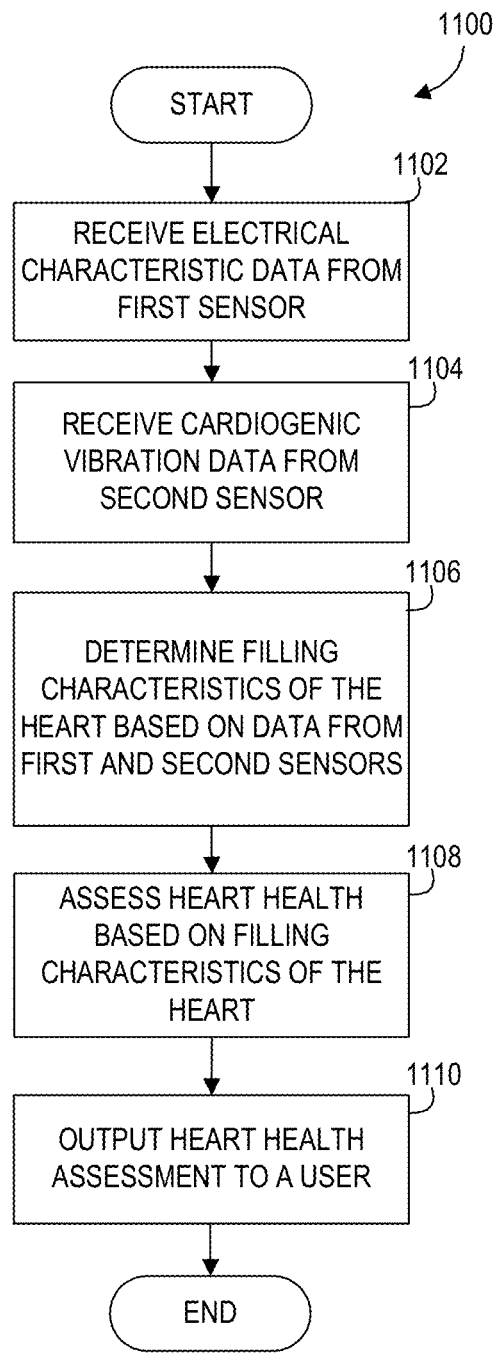
FIG. 11 provides a flow chart illustrating an example method for assessing heart health, in accordance with the present disclosure.

The disclosed technology includes methods for assessing heart health, such as method 1100, which is illustrated in FIG. 11. Method 1100 and/or any other method described herein can be performed by a controller or computer. For example, the method 1100 can be performed by the wearable device 110 that includes a controller or computer. Alternatively, or in addition, the method 1100 can be performed by a remote controller or computer. For example, the wearable device 110 can connect (e.g., through a transceiver, through a memory card, through a plug 172 and wires) to a remote controller or computer.

The method 1100 can include receiving 1102 data from a first sensor. The data from the first sensor can relate to at least one electrical characteristic of the heart of a user. For example, the first sensor can measure an ECG signal of a user.

The method 1100 can include receiving 1104 data from a second sensor. The data from the first sensor can relate to cardiogenic vibrations of a user. For example, the second sensor can measure a SCG signal of a user. Alternatively, or in addition, the second sensor can measure a gyrocardiogram signal of a user.

The method 1100 can include determining 1106, based on data from the first and second sensors, filling characteristics of the heart. For example, the filling characteristics of the heart can be is based, at least in part one or more axes of a SCG signal (e.g., Lat, HtoF, DV). Alternatively, or in addition, the filling characteristics can be based, at least in part, on the SCG signal during a diastolic portion of a heartbeat.

The method 1100 can include assessing 1108, based on filling characteristics of the heart, heart health. For example, the assessment of heart health can include a classification of a clinical status of heart failure (HF) in the user. Alternatively, or in addition, the assessment of heart health can include data indicative of changes in filling characteristics of the heart of a user. For example, changes in hemodynamics, filling pressure, pulmonary artery (PA) pressure, pulmonary capillary wedge pressure (PCWP), and the like, or any combination thereof.

The method 1100 can include outputting 1110 the heart health assessment to a user. For example, the heart health assessment can be sent to a connected device (e.g., smart phone, tablet, computer). Alternatively, or in addition, the heart health assessment can be displayed on a heart health assessment device (e.g., a wearable device). The heart health assessment can include an alert to a user. For example, the method 1100 can be performed repeatedly and in real time and the heart health assessment can include an alert when the heart health assessment changes. By monitoring and alerting in real time, users and/or clinicians can treat patients with heart failure. For example, users and/or clinicians can intercept the bodies compensatory loop (e.g., through medicine titration).

Figure 12:
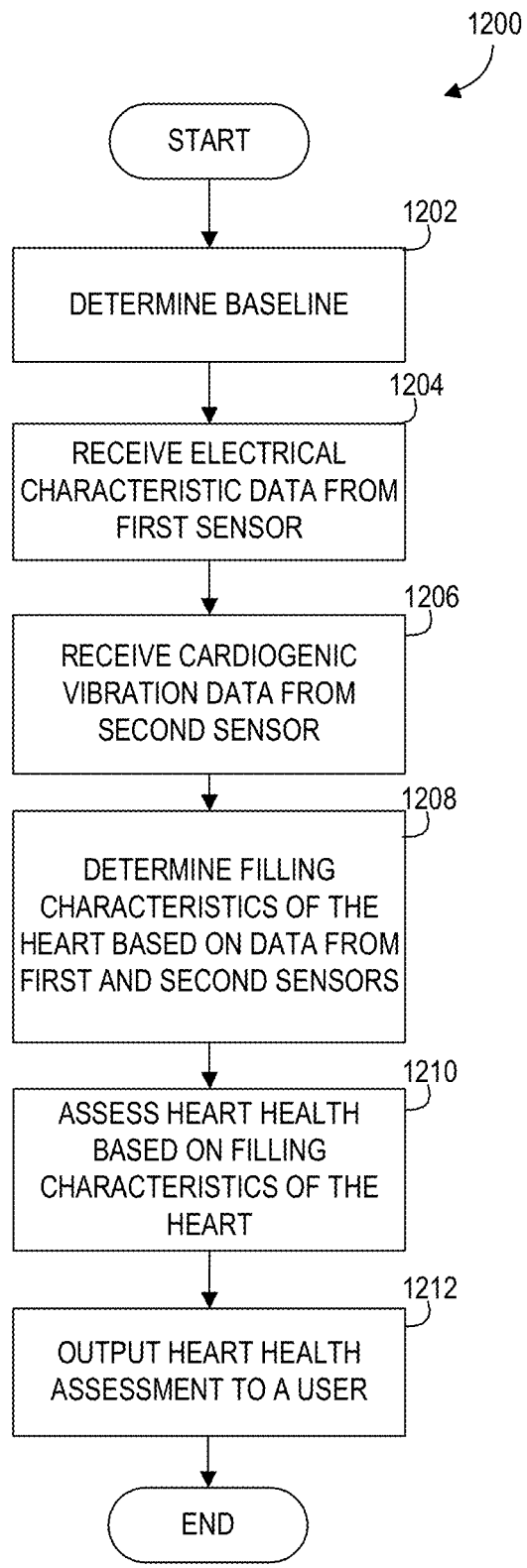
FIG. 12 provides a flow chart illustrating an example method for assessing heart health, in accordance with the present disclosure.

The disclosed technology includes method 1200 for assessing heart health, which is illustrated in FIG. 12. Method 1200 and/or any other method described herein can be performed by a controller or computer. For example, the method 1200 can be performed by the wearable device 110 that includes a controller or computer. Alternatively, or in addition, the method 1200 can be performed by a remote controller or computer. For example, the wearable device 110 can connect (e.g., through a transceiver, through a memory card, through a plug 172 and wires) to a remote controller or computer.

The method 1200 can include determining 1202 a baseline. For example, determining 1202 a baseline can include calibrating the system 100 with a baseline. The baseline can be a baseline filling pressure. The baseline can be determined based on a population-level baseline. For example, baseline pulmonary pressure values, can be tracked using features from noninvasive SCG and ECG signals using population-level regression algorithms. Alternatively, or in addition, the baseline can be determined based on a personalized baseline. The personalized baseline can be determined based on data collected from an RHC procedure. For example, a personalized baseline can be determined based, at least in part, on pressure values obtained from an RHC apparatus. Alternatively, or in addition, the personalized baseline can be determined based on data from a clinician.

For example, a personalized baseline can be determined based, at least in part, on pressure values obtained from a clinical exam.

The method 1200 can include receiving 1204 data from a first sensor. The data from the first sensor can relate to at least one electrical characteristic of the heart of a user. For example, the first sensor can measure an ECG signal of a user.

The method 1200 can include receiving 1206 data from a second sensor. The data from the first sensor can relate to cardiogenic vibrations of a user. For example, the second sensor can measure a SCG signal of a user. Alternatively, or in addition, the second sensor can measure a gyrocardiogram signal of a user.

The method 1200 can include determining 1208, based on data from the first and second sensors, filling characteristics of the heart. For example, the filling characteristics of the heart can be based, at least in part, on one or more axes of a SCG signal (e.g., Lat, HtoF, DV). Alternatively, or in addition, the filling characteristics can be based, at least in part, on the SCG signal during a diastolic portion of a heartbeat. Additionally, the filling characteristics can be based, at least in part, on the determined baseline.

The method 1200 can include assessing 1210, based on filling characteristics of the heart, heart health. Additionally, the assessment of heart health can be based, at least in part, on the determined baseline. The assessment of heart health can include a classification of a clinical status of HF in the user. Alternatively, or in addition, the assessment of heart health can include data indicative of changes in filling characteristics of the heart of a user. For example, changes in hemodynamics, filling pressure, PA pressure, PCWP, and the like, or any combination thereof.

The method 1200 can include outputting 1212 the heart health assessment to a user. For example, the heart health assessment can be sent to a connected device (e.g., smart phone, tablet, computer). Alternatively, or in addition, the heart health assessment can be displayed on a heart health assessment device (e.g., a wearable device). The heart health assessment can include an alert to a user. For example, the method 1200 can be performed repeatedly and in real time and the heart health assessment can include an alert when the heart health assessment changes. By monitoring and alerting in real time, users and/or clinicians can treat patients with heart failure. For example, users and/or clinicians can intercept the bodies compensatory loop (e.g., through medicine titration).

The methods 1100 and 1200 can further include receiving data from one or more additional sensors. For example, the methods 1100 and 1200 can include receiving data from a third sensor. The third sensor can be configured to measure environmental parameters. For example, the third sensor can be configured to measure one or more of temperature, humidity, altitude, and the like, or any combination thereof. Alternatively, or in addition, the third sensor can be configured to measure a photoplethysmography signal of the user. The methods 1100 and 1200 can include receiving data from a third sensor and a fourth sensor. For example, third sensor can be configured to measure environmental parameters and the fourth sensor can be configured to measure a photoplethysmography signal of the user.

The following examples further illustrate aspects of the present disclosure. However, they are in no way a limitation of the teachings or disclosure of the present disclosure as set forth herein.

EXAMPLES

Example 1

The following example uses signal processing and machine learning algorithms to extract relevant information from noninvasive cardiovascular electromechanical signals measured with our unique wearable patch hardware to estimate intracardiac and pulmonary pressures.

This example comprises a wearable device that receives signals representative of biological functions (for example, filling pressures of the heart), and methods of processing the information contained in the signals to, for example, estimate filling pressures from ECG and SCG signals.

In this example, we developed signal processing and machine learning algorithms to extract relevant information from noninvasive cardiovascular electromechanical signals measured with our unique wearable patch hardware to estimate intra-cardiac and pulmonary pressures. We have collected simultaneous single-lead ECG and tri-axial SCG signals using a custom-built wearable patch from patients with HF undergoing RHC, a gold-standard clinical procedure to measure intra-cardiac and pulmonary pressures. We have estimated the baseline pressure values (obtained from the RHC apparatus) using the features from simultaneously recorded SCG and ECG signals, as well as the changes in those pressures for a subset of subjects/patients who underwent pharmacological challenge during the RHC procedure.

Baseline pulmonary pressure values as well as the changes in pressures, can be tracked using features from noninvasive SCG and ECG signals using population-level regression algorithms. An unobtrusive wearable patch-based wearable device and corresponding signal processing and machine learning algorithms capable of tracking the filling pressure of the heart via measuring the pulmonary pressures can enable remote home monitoring for patients with HF and other cardiovascular diseases. With remote monitoring of HF patients, titration of care at home is possible which can ultimately reduce hospitalizations and improve the quality of life of the affected individuals.

The wearable patch hardware has a unique combination of ECG, SCG, and environmental sensing capability, which allows for context-aware determination of hemodynamic parameters in unsupervised settings. Compared to other technology which only measures electrophysiology, or other wearable systems that might measure SCG signals as well, the measurement of environmental parameters such as altitude, humidity, and temperature allow for the estimated hemodynamic parameters such as PCWP or pulmonary artery pressure (PAP) to be put in the context of activity and/or environment. For example, vasodilation in the heat will lead to relative hypovolemia in the cardiovascular system, thus resulting in a decrease in preload (decrease in PCWP and PAP); adding these environmental features together with the SCG and ECG features for the machine learning based model estimating hemodynamic parameters will be more accurate.

Moreover, we focus in part of our work on estimating changes in PAP and PCWP resulting from a perturbation—while pharmacological perturbation (vasodilator delivery) is used as an example, such perturbation could also be resulting from exercise, changes in ambient temperature (e.g., heat induced vasodilation), changes in posture (e.g., sit to stand based changes in preload), or other modulation techniques based on electrical stimulation of peripheral nerves or other changes in the baseline physiological state. Such a technique can be used, for example, to calibrate the hemodynamic parameters. Rather than measuring the signals at rest only, the signals can be measured before and after such a perturbation, and the direction or magnitude of physiological changes induced by the perturbation could be incorporated in the algorithms for improving the accuracy of PAP, PCWP and other internal hemodynamic parameters to be estimated.

We have developed signal processing and machine learning algorithms to track the filling pressure (preload) of the heart by extracting relevant features from wearable ECG and SCG signals. We have collected data (single-lead ECG and tri-axial SCG) using a custom-built wearable chest patch. Tracking the filling pressure of the heart and taking proactive measures (medication titration, follow-up hospital visits, etc.) have shown efficacy in reducing hospitalization for HF-related complications and all-cause hospitalization for patients with HF. However, the high cost associated with devices used in the clinic and at-home settings to track the filling pressure of the heart precludes their usage in the large patient population affected by HF. The wearable sensor and corresponding algorithm that we are developing can be a low-cost alternative to the high-cost hemodynamic monitoring systems.

We have shown for the first time that the filling pressure of the heart can be tracked using SCG and ECG signals. We were able to estimate the baseline pressure values at different intracardiac and pulmonary chambers (PA, pulmonary capillaries, right atrium, and right ventricles). We have also developed an algorithm to track changes in these pressures with pharmacological perturbation (e.g., infusing vasodilator). For the baseline pressure estimation, the patient was in supine position as still as possible for at least ten minutes. During this baseline recoding period, the patient might have some involuntary movements that distort the SCG signals. We developed an algorithm to detect and reject motion contaminated SCG signals. Using signal quality indexing (SQI), we stratified the patient's high-quality SCG heartbeats. From the high-quality SCG heartbeats, we extracted relevant features from each axis of the SCG, including DV, Lat, HtoF, and magnitude of all three axes of the SCG signal. On top of these features, we trained a population regression model to predict the mean pressure values. The model was validated using a leave-one-subject-out cross-validation method.

For tracking the changes in the pressures, we developed a dynamic time warping (DTW) based distance metric to estimate the changes in SCG from a baseline state to vasodilator infused state and used these DTW distances from different portions (systolic and diastolic) and different axes (HtoF, Lat, DV and overall magnitude) of the SCG signals to estimate the changes in the pressures (PA, pulmonary capillaries, right atrium, and right ventricles). We have developed algorithms to remove outlier heartbeat signals and signals with low quality (due to motion artifacts and other reasons) using a dimensionality reduction technique (principal component analysis) and a Gaussian mixture model. We have developed global regression models (e.g., Ridge, Lasso, Random Forest, etc.) to estimate the changes in pressure values with corresponding DTW distances from the SCG signals and validated our model with leave-one-subject-out cross-validation.

Most of the research with SCG focuses on the systolic portion and DV axis of the signals. However, in our work, we have demonstrated that features from the diastolic portion of the signals, and Lat axis and overall magnitude of the signal provides salient/valuable information besides the DV direction during the systolic portion of the SCG signal, regarding the changes in intracardiac and pulmonary pressures.

The algorithm may include other metrics to estimate the changes in SCG signals from one state to another with underlying changes in hemodynamics, Euclidean distances, Mahalanobis distances, clustering-based unsupervised learning approach, deep learning models as well. To improve the signal quality and have reliable feature extraction, different other methodologies can be used, including manifold mapping, clustering, etc. The algorithm may include the variation in the SCG signals to track the changes in hemodynamics during activities of daily living as well, which may provide information regarding exercise intolerance, which is used to stratify risks associated with HF. In this disclosure, we estimated changes in the pressure on the right side of the heart (right atrium, right ventricles), PA, and pulmonary capillaries. The algorithm may be translated to the changes in the pressure on the left side of the heart (left atrium, left ventricle), and aorta.

These examples present a wearable, inexpensive, minimally obtrusive system to remotely monitor HF patients using wearable seismocardiography (SCG). The SCG signal captures the vibrations of the chest wall in response to cardiac ejection of blood and heart movement. We investigate the use of SCG signals to classify clinical status of HF patients in a baseline state and the ability of SCG features to accurately estimate filling pressure. Specifically, in this work, we demonstrate accurate classification of clinical status of HF patients in a resting state with an area under the curve (AUC) of 0.8. Moreover, we disclose a machine learning based regression model to measure PCWP, an indirect measurement of left atrial pressure similar to PA pressure. The ability to measure PCWP provides valuable information to caregivers similar to implantable devices that measure PA pressure. All the data in this work was collected in the cardiac catheterization laboratory to acquire both SCG signals and hemodynamic parameters while patients were undergoing RHC.

Subject Demographics, Experimental Protocol, and Sensing Hardware

A. Data Collection and Experimental Protocol

A total of 50 subjects diagnosed with HF were enrolled in the study. Exclusion criteria included implanted ventricular assist devices and prior heart transplantation. Demographics of the study population are shown in TABLE I. Each subject provided written informed consent before the data collection.

TABLE I

Demographic Information of Subjects

| | Gender | | NYHA Class | | | |
|---|---|---|---|---|---|---|
| | Male | Female | I | II | III-IV | Overall |
| # Patients | 34 | 16 | 4 | 9 | 37 | 50 |
| # Comp. Recordings | 16 | 13 | 4 | 5 | 20 | 29 |
| # Decomp. Recordings | 19 | 3 | 0 | 4 | 18 | 22 |
| Age ($\mu \pm \sigma$) | 56.9 13.7 | 52.6 14.9 | 61.5 16.7 | 55.0 15.1 | 55.0 13.8 | 55.5 14.1 |
| Height ($\mu \pm \sigma$, in cm) | 176.3 8.2 | 164.8 6.9 | 177.1 8.6 | 170.2 7.2 | 172.7 10.0 | 172.6 9.4 |
| BMI ($\mu \pm \sigma$, in kg/m$^2$) | 29.2 7.3 | 26.2 9.9 | 23.5 13.2 | 28.0 12.2 | 28.2 7.6 | 28.8 7.3 |

The aim of the protocol was to explore the discriminative features of SCG in differentiating clinical status (i.e., decompensated and compensated states) of HF patients in a baseline state (i.e., at rest) and the correlation between SCG and hemodynamic parameters. To determine the clinical status and capture the hemodynamic parameters, RHC was performed using the Mac-Lab Hemodynamic Recording System. Based on the RHC procedure, the following hemodynamic parameters were measured: cardiac index (CI), PCWP, PAP, right atrium pressure (RAP) and right ventricle pressure (RVP). Based on the hemodynamic parameters, clinical status was determined as follows: if a patient had a mean PCWP of 20 mmHg or more and a CI of 2.2 L/min/m² or less, the patient was considered decompensated. Otherwise, the patient was considered compensated. In some rare cases, this rule was overridden by the caregivers if one of the PCWP or CI values were unusually high/low. For example, a patient with borderline PCWP of 16 mmHg combined with extremely low CI of 1.3 L/min/m² was considered decompensated.

All the SCG data was collected while patients were undergoing the RHC procedure. The patient, firstly, rested supine on a procedure table. The wearable patch hardware was attached to the mid-sternum of the patient to acquire SCG signals. During the procedure, the patient was instructed to remain as still as possible. Then, the catheter was inserted into the patient's body to measure the hemodynamic parameters. The supine position and the motionless state of the patient is referred to herein as the baseline state. We refer to all the signals collected during a single RHC procedure as a recording, which consists of ECG and SCG signals from the wearable patch and pressure waveforms from the Mac-Lab Hemodynamic Recording System. Moreover, we define compensated recording as a recording acquired from a patient who is determined to be compensated and similarly for decompensated recording. TABLE I shows the number of compensated and decompensated recordings in the collected dataset. Note that one patient underwent RHC procedure twice and thus the number of recordings is one more than the number of patients. The data collection setup, along with example signal excerpts, is illustrated in FIG. 1E. FIG. 1E provides an illustration of a data collection setup. The HF patient is in a supine position while undergoing RHC procedure. During the procedure, a wearable patch is attached to the mid-sternum of the patient to collect ECG and SCG signals. On the right-hand side, an example set of representative ECG and SCG signals is shown, collected from wearable SCG patch, along with RHC waveforms, collected from Mac-Lab Hemodynamic Recording System. The waveforms are in their unfiltered raw form.

B. Sensing Hardware

The wearable patch samples the ECG signal at 1 kHz, the accelerometer signals at 500 Hz and the environmental signals at 20 Hz, and saves the data into a micro secure digital (microSD) card in the patch. A custom-built graphical user interface transfers all the data from the microSD card to a computer and resamples the accelerometer and environmental signals at 1 kHz such that all signals share the same sampling rate for ease of processing. All signals are then decimated to 500 Hz in our processing algorithms for further analysis.

Signal Processing and Machine Learning Methods

A. Signal Preprocessing

The first preprocessing step is to remove five minutes from the beginning and the end of each recording, since in some recordings the sensor starts recording before the device is attached to the subject and ends recording after device is detached. As a second step, we band-pass filter the signals with the following digital filter specifications: finite impulse response (FIR) filter with pass band of 4-25 Hz and 1-40 Hz for ECG and SCG signals respectively and 80 dB attenuation in the stopbands. Resulting equiripple FIR filters had order 332 and 1407 for ECG and SCG signals, respectively. The pass band for the ECG signal was chosen as to isolate the Rpeaks for easier detection of them in the next processing step. For the SCG signal, the pass band was chosen to suppress out-of-band noise and preserve the SCG signal characteristics.

After filtering both the ECG and SCG signals, we formed an additional channel of SCG that we refer to as the magnitude channel.

$$SCG_{Mag}[n] = \sqrt{SCG_x[n]^2 + SCG_y[n]^2 + SCG_z[n]^2} \quad \text{Equation 1:}$$

Where $SCG_x[n]$, $SCG_y[n]$ and $SCG_z[n]$ are left-right, HtoF, and DV channels of SCG, respectively.

As a final pre-processing step, we detected R-peaks in the ECG signal and subsequently performed beat segmentation in SCG signals. For R-peak detection, we used two algorithms: Pan-Tompkins, implemented by Physionet, and the Phasor Transform, with a custom implementation. We only selected R-peaks that were detected from both algorithms to reduce false positives in R-peak detection. For detection, we used 12 second windows to detect the R-peaks.

Using the R-peaks, beat segmentation of SCG signal was carried out in the following way: 200 ms before the R-peak and 700 ms after the R-peak was delimited as the start and end of a beat, respectively. As a result, we constructed SCG beat arrays for each channel of SCG. Note that, in contrast to other prior work that typically performs beat segmentation from the Rpeak (i.e., 0 ms before/after the R-peak) to approximately 700 ms after the R-peak, in this work we deliberately included ventricular diastolic timing since we expected that the features observed during this time may be quite relevant for estimating filling pressures.

B. Motion Artifact Rejection and SQI

SCG signals are susceptible to motion artifacts: when a subject moves, SCG vibrations are contaminated by higher amplitude motion artifacts. In the collected dataset, even though patients were instructed to remain as still as possible, motion artifacts were still present in recordings. FIG. 3 illustrates examples of such artifacts in one recording. FIG. 3 provides an illustration of motion artifact rejection on the DV channel of SCG with FIG. 3A showing the full recording obtained from one representative subject, FIG. 3B showing a zoomed in visualization of the recording with a segment contaminated by a motion artifact, FIG. 3C showing an illustration of the most similar consecutive two beats in the recording, and FIG. 3D showing an illustration of the motion artifact corrupted beats in the full recording, with beats 310 indicating the samples where the magnitude channel exceeds the threshold.

By leveraging the observation that motion artifacts are of higher amplitude than SCG vibrations, we devised a simple algorithm to detect motion-corrupted SCG beats and subsequently discard motion-contaminated SCG beats. This algorithm inputs the segmented beat array and outputs the indices of motion-contaminated beats. The pseudo-code is shown in Algorithm 1. The key to the detection is the search for two consecutive beats that are the most similar. If the two consecutive beats are not contaminated by motion, they should be similar in morphology because in a short period of time we do not expect a substantial change in SCG morphology. The most similar two consecutive beats, therefore, should be free of motion artifacts (see FIG. 3C for an example of the most similar two consecutive beats in this recording). By computing a simple threshold using the motion artifact free part of the recording, we detect the motion artifacts as outlined in Algorithm 1. The result of the motion artifact detection algorithm is illustrated in FIG. 3.

---

Algorithm 1 Motion Artifact Detection

---

```
 1: procedure DETECTMOTIONARTIFACT(SCG_x, SCG_y,
         SCG_z, SCG_Mag)
 2:    inds ← [ ]                    ▷ Initialize empty list
 3:    j ← CompSimBeats(SCG_x, SCG_y, SCG_z)  ▷
         Find two consecutive beats that are the most similar
 4:    θ ← 1.5 times the range of values in the beats indexed
         by j in the magnitude channel.  ▷ Compute motion artifact
         threshold
 5:    for each beat in SCG_Mag do
 6:        if any sample of the current beat > θ then
 7:            add the beat index to the list inds
 8:        end if
 9:    end for
10:    return inds
11: end procedure
12: procedure COMPSIMBEATS(SCG_x, SCG_y, SCG_z)
13:    maxSim ← 0
14:    for each two consecutive beats (i, i+1) in SCG_x,
         SCG_y, SCG_z do
15:        sim X ← Similarity(b⃗^i_x, b⃗^{i+1}_x)
16:        sim Y ← Similarity(b⃗^i_y, b⃗^{i+1}_y)
17:        sim Z ← Similarity(b⃗^i_z, b⃗^{i+1}_z)
18:        if average(simX, simY, simZ) > maxSim then
19:            max Sim ← average(simX, simY, simZ)
20:            j ← [i, i + 1]
21:        end if
22:    end for
23:    return j
24: end procedure
```

---

To measure the similarity between two beats, the following formula was used:

$$\text{Similarity}(\vec{b_1}, \vec{b_2}) = 1 - \frac{\left\| \frac{\vec{b_1}}{\|\vec{b_1}\|_\infty} - \frac{\vec{b_2}}{\|\vec{b_2}\|_\infty} \right\|_2}{2\sqrt{M}} \quad \text{Equation 2}$$

where $\vec{b_1}, \vec{b_2} \in \mathbb{R}^M$. The range of values that the output of this formula can yield is between 0 and 1. If the output is closer to 1, the inputs are more similar and if the output is closer to 0, inputs are more dissimilar.

After motion artifact contaminated beats are detected and rejected, SQI, was applied separately to each channel of SCG to extract high quality SCG beats. Compared to the way SQI has been applied, we have the following differences: 1) There is no population of templates, rather we have one template per each channel for a recording; and 2) As a template, we used the ensemble average of the beats using Woody's method. With these changes, the template was tailored for the specific recording and without any motion artifact. As the output of SQI, quality scores for each beat were returned. We used the top 5% of the beats to extract features.

C. Feature Extraction

We used the output from SQI in two ways: 1) we computed an ensemble average of the beats; and 2) we used statistical features derived from each individual beat. From a single beat, we extracted the base features listed in TABLE II. When we used the ensemble averaged beat to extract the features listed in TABLE II, we essentially captured features related to the baseline SCG. We then extracted the baseline features from each one of the beats outputted from SQI. We then computed the following statistical features: mean, median, standard deviation, maximum and minimum. With this approach, we captured beat-to-beat changes. The time windows in the table were chosen in a way to reflect ventricular diastolic (−200 ms to 0 ms and 300 ms to 600 ms) and systolic (−50 ms to 250 ms) regimes of the cardiac cycle.

TABLE II

Extracted Base Features from a Beat

| Function Name | Windows Applied (0 ms is the R-peak) | Description |
|---|---|---|
| Power | All<br>−50 ms:250 ms<br>−200 ms:0 ms<br>300 ms:600 ms | Computes the power within the specified windows. |
| Max Amplitude | All<br>−50 ms:250 ms<br>−200 ms:0 ms<br>300 ms:600 ms | Computes the maximum amplitude within the specified windows. |
| Min Amplitude | All<br>−50 ms:250 ms<br>−200 ms:0 ms<br>300 ms:600 ms | Computes the maximum amplitude within the specified windows. |
| Delay of Max Amplitude | All<br>−50 ms:250 ms<br>−200 ms:0 ms<br>300 ms:600 ms | Computes the delay of the maximum amplitude within the specified windows. |
| Delay of Min Amplitude | All<br>−50 ms:250 ms<br>−200 ms:0 ms<br>300 ms:600 ms | Computes the delay of the minimum amplitude within the specified windows. |

To capture the possible relationship between diastolic and systolic intervals, features from two windows were also combined to form new features: for all the power and amplitude features the ratio between the systolic interval (−50 ms to 250 ms) to the diastolic interval (300 ms to 600 ms) was computed; for all the delay-related features, absolute differences between the systolic delays and diastolic delays were computed. We also aimed to capture features that carried crosschannel information. To this end, for all the pairs of channels (HtoF, DV and Lat) the ratio (amplitude and power features) and absolute difference (delay features) of the base features were computed, only across systolic and diastolic time windows, to form the new cross-channel features. In the end, a total of 690 features are extracted from a recording.

Figures 2A, 2B, 2C:
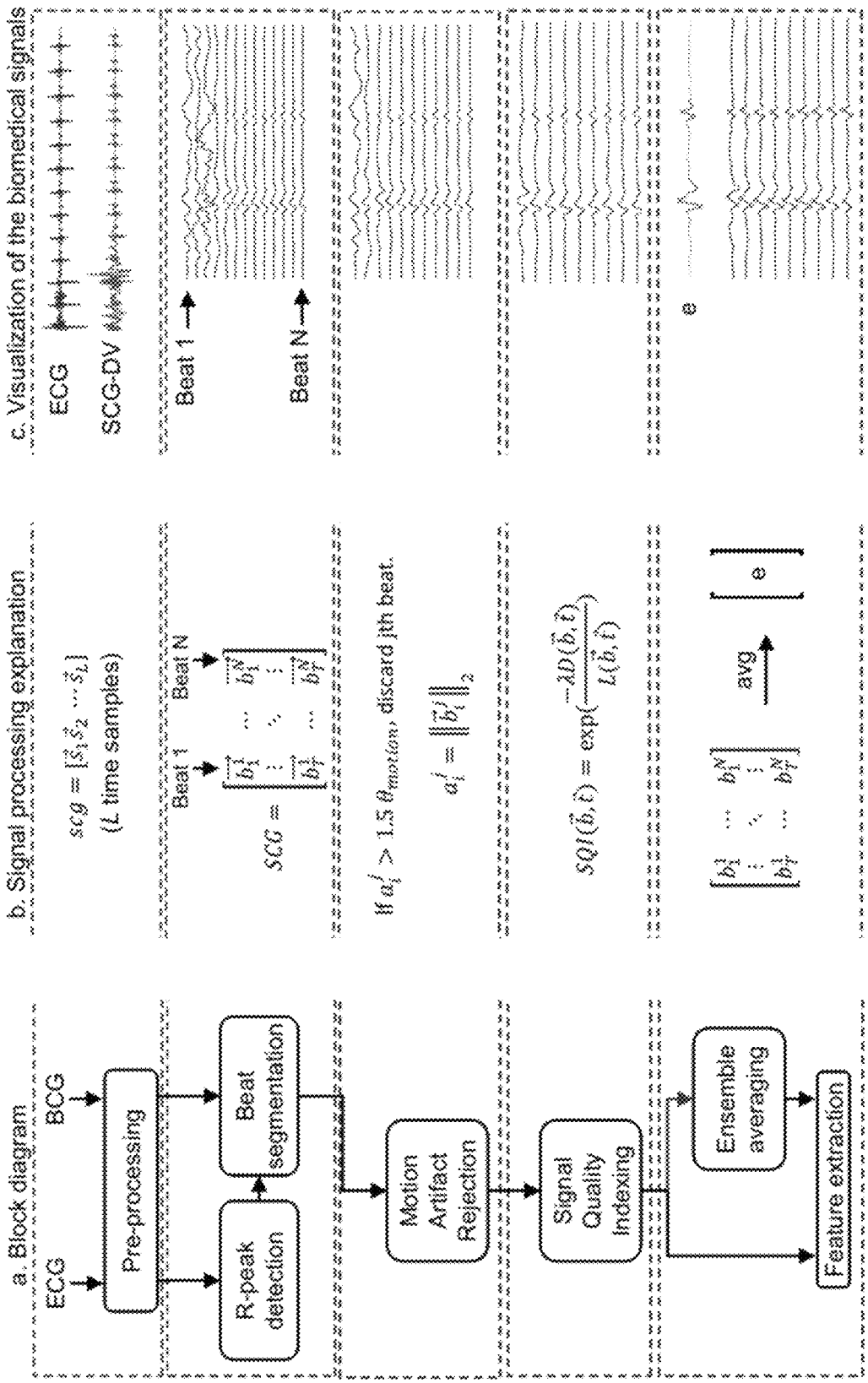
FIG. 2A provides a diagram of a method of processing data, in accordance with the present disclosure.
FIG. 2B provides a diagram of steps used for a method of processing data.
FIG. 2C provides a visualization of a method of processing data.

FIG. 2 provides an of the processing of the wearable patch data. FIG. 2A provides a block diagram representation of the processing. FIG. 2B provides a brief mathematical explanation of the steps used for the processing. FIG. 2C provides visualizations of the processing from a 10 s window of data from a representative participant. In the visualizations, only the DV channel of the SCG is shown for ease of visualization; other SCG channels undergo the same processing.

D. Classifier and Regression Algorithm Design

In this work, we used support vector machines (SVM) for both classification and regression tasks. SVMs search for a separating hyperplane to discriminate two classes. With kernels, SVMs can model non-linear relationship in the data. In this work we consider, polynomial and radial basis function (rbf) kernels. Additionally, for the regression task, we consider linear regression with lasso.

E. Experiment Design

The first goal in the experiments was to analyze the capability of SCG features to discriminate HF clinical status. To this end, we treated the problem as binary classification where the input was SCG features and the output was whether the patient was in a decompensated or compensated state. To evaluate the classification models, we performed leave-one-subject-out cross validation (LOSOCV) to compute classification accuracy and the AUC of ROC curve. After evaluating the models which uses all the extracted features, sequential forward feature selection (SFFS) is performed. SFFS helps in addressing the curse of dimensionality, as there were more features extracted (690) than data points (51). Additionally, SFFS is informative in which features are more important in the classification.

In the previous two experiments, each recording, varying in length from 25 minutes to 200 minutes, was treated as a single data point for classification. To address the minimum length of a recording that can be still accurately classified, each recording was broken down into non-overlapping windows of one, five, ten, 15, 20 and 25 minutes. In each window, features were extracted according to the same methodology outlined in these examples as this feature extraction is invariant of recording length. Using the best performing features and hyperparameters from the previous two experiments, we again used LOSOCV to evaluate the performance at different windows.

As a final experiment, we estimated the mean PCWP from SCG features using a regression algorithm, with the input comprising extracted features from a recording and the output being the mean PCWP value from RHC. Again, LOSOCV was used to evaluate the regression models. As a performance metric, we used root mean squared error (RMSE) between the regression output and the ground truth value measured during the RHC procedure. Similar to the classification experiments, we performed an SFFS.

Experimental Results

A. Classification Experiments

Figure 4:
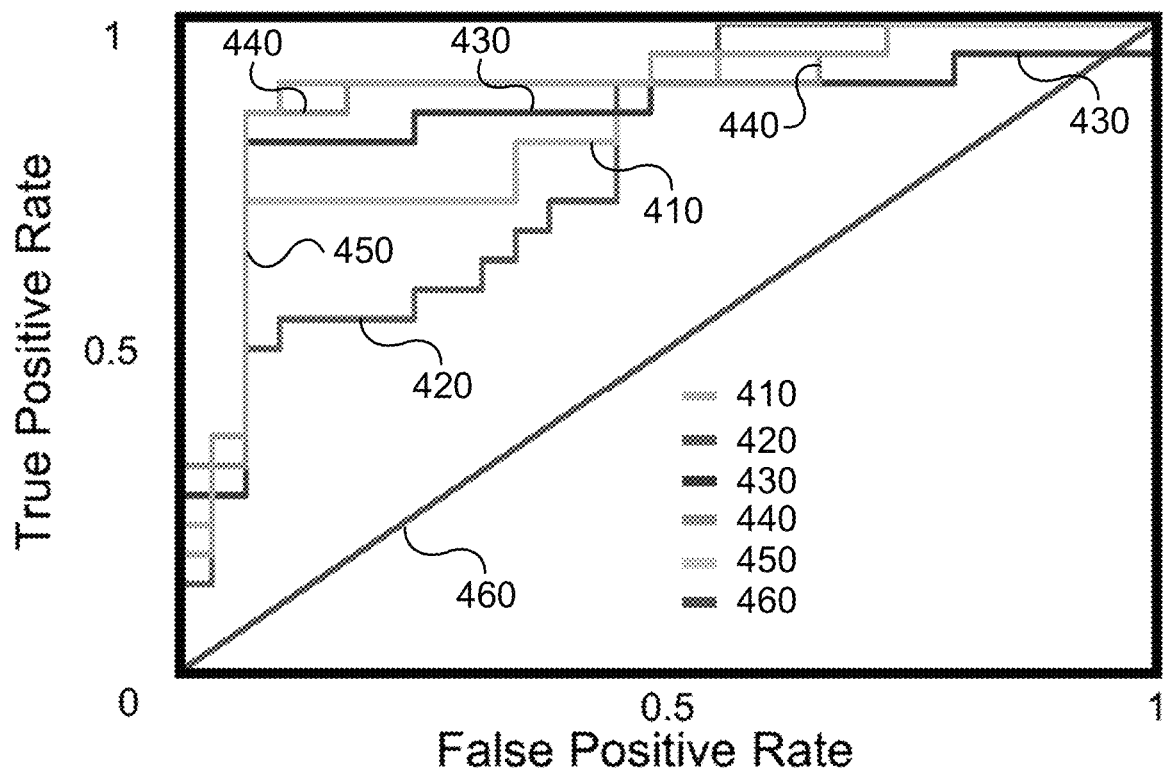
FIG. 4 provides a graph of classification experiment results, in accordance with the present disclosure.

The classification experiment results are presented in TABLE III and FIG. 4. FIG. 4 provides receiver operation characteristics (ROC) curves for different classifiers trained and tested (using best feature 410; using all features 420; using three features 430; using four features 440; using five features 450; random chance 460). The 420 curve is the ROC curve of the RBF kernel SVM that is used in the SFFS. Based on these results, using smaller number of features improves performance as expected because of curse of dimensionality.

TABLE III

Classification Performance for Classifiers Performing LOSOCV

|  | Linear SVM | Polynomial SVM | RBF SVM |
| --- | --- | --- | --- |
| Accuracy | 0.71 | 0.73 | 0.75 |
| AUC | 0.73 | 0.73 | 0.69 |

Figure 5:
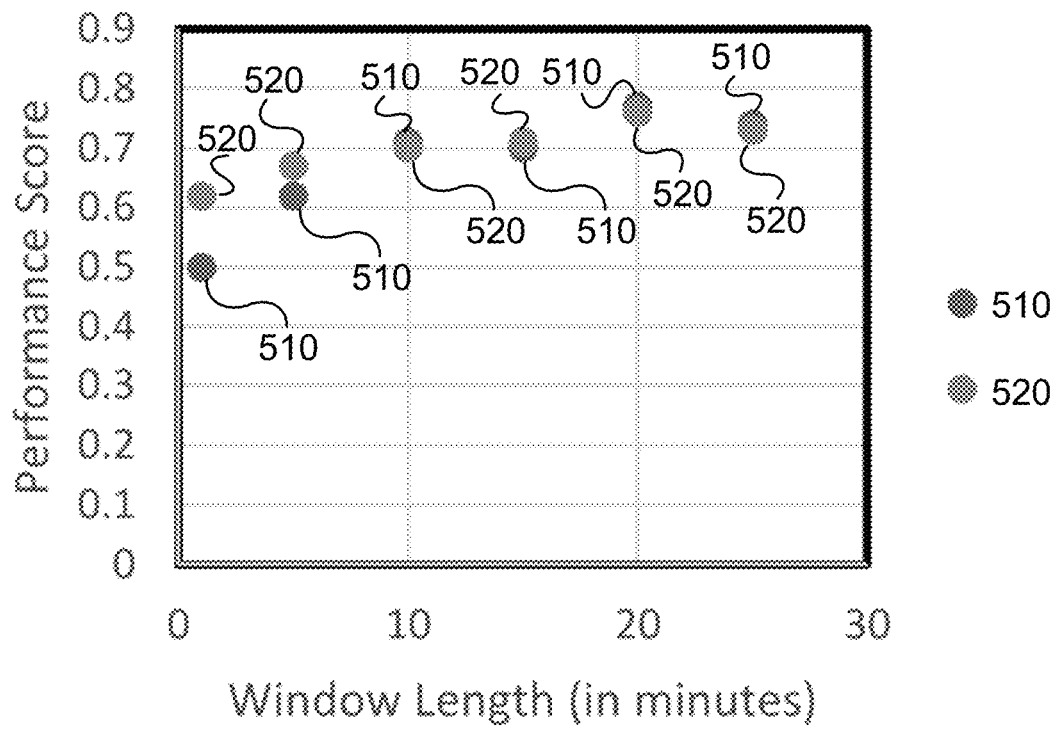
FIG. 5 provides a graph of windowing experiment results, in accordance with the present disclosure.

The results from windowing experiments are presented in FIG. 5. FIG. 5 provides performance of the best classifier under different window lengths showing AUC 510 and accuracy 520. According to these results, Degradation in the performance of the classifier is observed with smaller window length until ten minutes. After ten minutes of recording, performance plateaus.

B. Regression Experiments

The results from the regression experiments are presented in TABLE IV. Similar to the classification experiments, model trained using SFFS outperforms other models.

TABLE IV

Regression Performance of Various Models Under LOSOCV

|  | Linear SVR | Polynomial SVR | RBF SVR | Linear Regression + LASSO | SFFS |
| --- | --- | --- | --- | --- | --- |
| RMSE (mmHg) | 7.03 | 7.02 | 7.03 | 8.12 | 3.41 |

Discussion

The results in FIG. 4 and TABLE III disclose that accurate classification of HF patients can be achieved using SCG features. Moreover, using a small subset of SCG features improves the performance. This secondary result is expected as there are many more features extracted than the number of data points. Currently, the clinical status of HF patients for physiological decompensation requires catheterization, which is expensive and invasive. This wearable device can accurately classify clinical status and can be used as a pre-screening tool to reduce the number of RHC procedures, which can reduce HF care costs and improve quality of life.

The result in FIG. 5 demonstrates that when using shorter recordings the performance decreases. As the recording length is increased, performance improves until it reaches a plateau. Based on these results, at least ten minutes of SCG data should be obtained achieve meaningful performance. This information is important for determining how long the device must be on the patient before clinical status is determined.

The results of the regression experiments are promising for SCG signals. The ability to predict the mean PCWP from SCG signals could greatly impact HF care at home. Measuring PCWP daily, or more frequently if desired, with this wearable device can allow a filling pressure guided therapy similar to the approach used in an implantable filling pressure monitor. Importantly, by providing this parameter rather than a black box output driving a decision, physician can be kept in the loop and care could be titrated as desired based on existing flow charts and guidelines.

Additionally, the features selected in the experiments provide important scientific insight into SCG signals, which are not as well understood as ECG signals, for example. We observed that the top five features of the best performing classifier were derived from both DV (1) and Lat (4) channels, thus demonstrating the importance of analyzing all axes of SCG signal data rather than just DV. Moreover, for the regression problem the top performing two features were also derived from the lateral channel of the SCG.

These examples further include a low-cost system that can track changes in hemodynamic congestion has the potential to help millions of people affected by HF. The increased intracardiac filling pressure provides an early and actionable indication of the onset of congestion in HF. Hemodynamic changes precede progression of chronic compensated HF to acute decompensated HF (ADHF) by several week. Recent research also shows that the product of small changes in pulmonary pressure over an extended period of time is closely associated with the transition to ADHF. Accordingly, tracking hemodynamics using an implantable hemodynamic congestion monitoring system and subsequent proactive HF management therapies (e.g., titration of medications, early follow-up clinic visits, etc.) to reduce subclinical congestion have demonstrated efficacy in reducing HF-related rehospitalization. Compared to hemodynamically-guided HF management, traditional HF management therapies including tracking of daily weights, telemonitoring vital signs, and clinical symptoms to detect ADHF have not shown efficacy in reducing HF-related rehospitalization in large randomized controlled trials, as these changes occur comparatively later into the progression from compensated HF to ADHF.

Seismocardiography (SCG), the local mechanical vibration of the chest wall associated with the movement of the heart and blood within the vasculature, can be used to monitor cardiovascular health. SCG timings can be used to assess changes in cardiac contractility via estimating the pre-ejection period of the heart, with exercise and physiological perturbation. Importantly, SCG can be used to assess the clinical status of patients with decompensated HF. Besides the assessment of clinical status in patients with HF, SCG has exhibited efficacy in tracking instantaneous oxygen uptake during cardiopulmonary exercise tests in patients with HF and uncontrolled daily life activities in healthy individuals. Based on these results in tracking hemodynamics with SCG for both healthy individuals and patients with HF, changes in hemodynamic congestion can be tracked with the simultaneously recorded SCG signal via estimating changes in PAP and PCWP.

Methods

SCG and ECG signals were recorded from patients with HF using a custom-built wearable patch during RHC, the gold standard of measuring hemodynamic congestion via PAP and PCWP. During the RHC procedure, the PAP and PCWP were modulated by infusing systemic vasodilators, and changes in the mean pressure values were estimated via tracking the changes in simultaneously recorded SCG signals. Various portions of the SCG signals were analyzed to understand the important segments that are providing salient information regarding changes in PAP and PCWP. Tracking acute changes in hemodynamic congestion with SCG can demonstrate the potential of using this novel wearable technology, an unobtrusive and low-cost alternative to the current monitoring systems, in longitudinal monitoring of the intracardiac filling pressures in remote HF management, and potentially ultimately reduce HF-related rehospitalization.

A. Experimental Protocol

RHC procedures were conducted on a total of 20 HF patients (eight inpatients and 12 outpatients) who were referred for hemodynamic evaluation of their HF. Patients in cardiogenic shock were excluded. The dataset was separated randomly into two groups of 15 HF patients for a training-testing set and five HF patients for a separate independent validation set (details in the supplementary materials section below).

FIGS. 1A-1C illustrate the experimental setup and placement of different sensors on each patient. FIG. 1A provides the experimental setup with a wearable patch placed on a subject undergoing RHC procedure, with axes (on the upper-right) showing the axes of the SCG signal. FIG. 1B provides a top, bottom, and inside view of a wearable patch. FIG. 1C provides a front (left) and side (right) view of a wearable patch placed on a representative subject. Before starting the RHC procedure, the custom-built wearable patch was placed just below the suprasternal notch, and the cath lab recording system was time-synchronized with the wearable patch.

The RHC procedure was carried out in a quiet, environmentally controlled cardiac catheterization laboratory with an ambient temperature of ~25° C. Right neck or right antecubital fossa regions were cleaned and prepped in a standardized sterile fashion using Chlorhexidine swabs. Local anesthesia was administered with 2% lidocaine. Under ultrasound guidance, venous access was obtained, and a 5 French (F) introducer sheath was placed in the right internal jugular or right brachial vein. After at least 20 minutes of rest in a supine position, a 6 F balloon-tipped PA wedge catheter was advanced under fluoroscopic guidance into the right atrium, right ventricle, pulmonary arterial, and pulmonary capillary wedge positions. At each position, pressures were acquired over 60 seconds during gentle end-expiratory breath-hold (end-expiration), repeated in triplicate and averaged, per standard RHC protocols. Cardiac output was obtained by the Fick principle and thermodilution. After baseline hemodynamics and cardiac output were measured, and after a ten-minute rest in a supine position, pharmacological agents were administered at the discretion of the HF physician performing the case. Nitroglycerin was given as sublingual spray (400 or 800 mcg), and nitroprusside was administered as intravenous (IV) infusion starting at 0.3 mcg/kg/min (and titrated by 0.3 mcg/kg/min every five minutes until a hemodynamic effect was achieved). At the peak hemodynamic effect as determined by the HF physician, the hemodynamics were repeated as per baseline protocol. Thereafter, the balloon-tipped PA wedge catheter and the venous sheath were removed.

The wearable ECG and SCG signals were recorded continuously throughout the RHC procedure, and the time-stamps from both the RHC and wearable system were used to extract the specific portions of the wearable signals later in the analysis, to estimate the changes in PAP and PCWP from the changes in wearable signals. FIG. 1D shows the wearable signals with corresponding PAP signal from the RHC computer during the baseline RHC recording from a representative subject. FIG. 1D provides representative cardiogenic signals: ECG, triaxial SCG (HtoF, Lat, and DV), and RHC PAP signal. SCG is a mechanical signal that has been associated with cardiac muscle contraction, cardiac valve movement, and movement of the blood from the left ventricle towards aorta.

B. Sensing Hardware

RHC pressure values were extracted from the cath lab Mac-Lab system. The wearable ECG and triaxial SCG (axes: HtoF, DV, and Lat) were collected, with a custom-built wearable patch as shown in FIG. 1B. The patch of this example has a diameter of 7 cm and a weight of 39 gm. All the wearable ECG and SCG signals were sampled at 1 kHz. FIG. 1D shows representative ECG and tri-axial SCG signals from the wearable patch.

C. Signal Processing and Feature Extraction

Figure 6A:
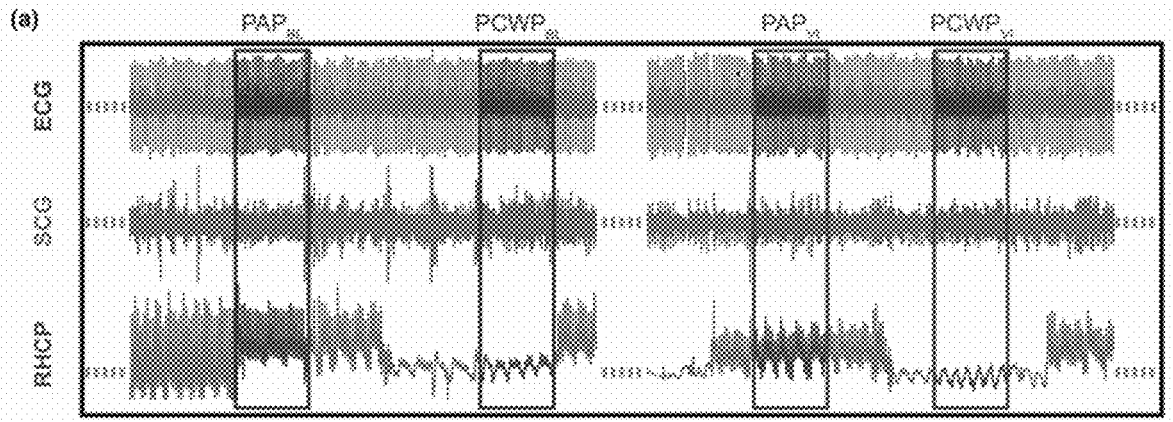
FIG. 6A provides example signal data from a system for assessing heart health, in accordance with the present disclosure.
Figure 6B:
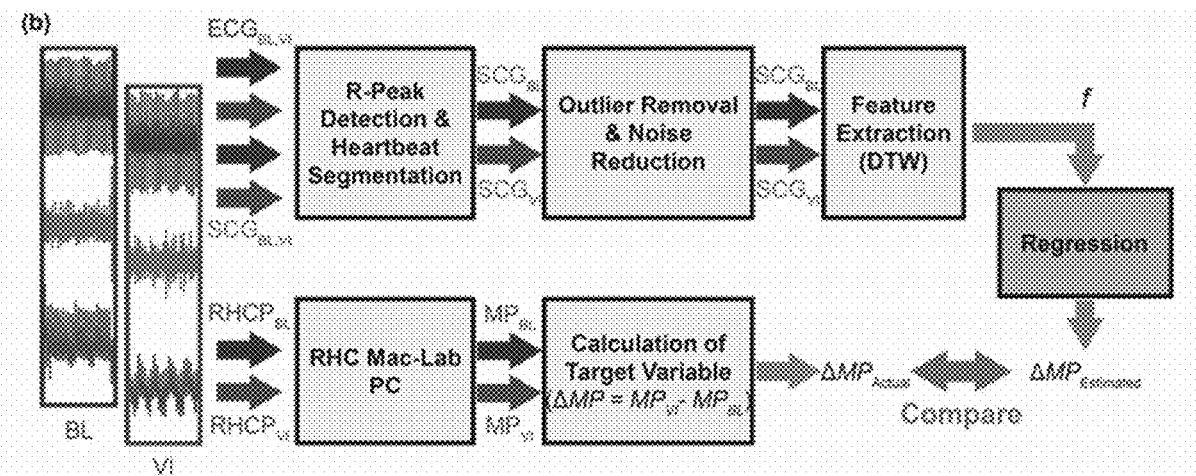
FIG. 6B provides a diagram of an example method for signal processing, in accordance with the present disclosure.
Figure 6C:
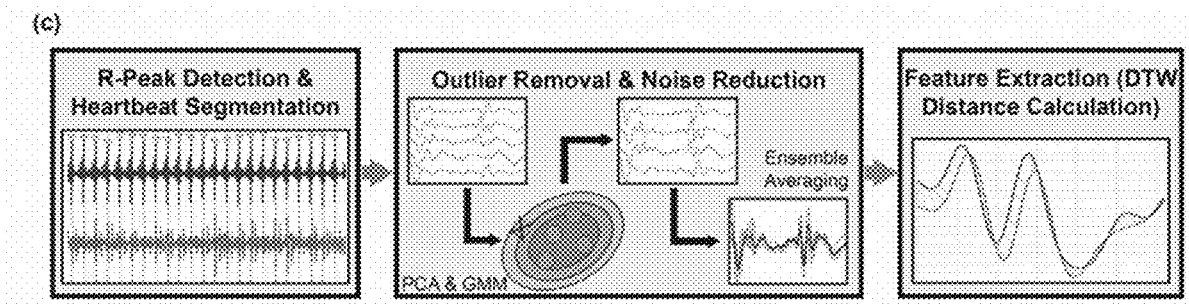
FIG. 6C provides a diagram of an example method for signal processing, in accordance with the present disclosure.

FIG. 6 illustrates the signal processing and feature extraction procedures used for the wearable signals and the pressure signal from the cath lab Mac Lab system. FIG. 6 provides an overview of the method. FIG. 6A provides wearable ECG and SCG (only showing one axis of the signal for simplicity) signals were synchronized with the right heart catheterization pressure (RHCP) signal. 20 seconds long signals from both baseline (BL) and during vasodilator infusion (VI) were extracted when the catheter was recording PA pressure and in pulmonary capillary wedge (PCW) pressure signals. FIG. 6B provides the R-peaks of the ECG signal were detected and later used to segment the corresponding SCG signals into individual heartbeats. Outlier removal and noise reduction steps were performed on the SCG heartbeats, and features were extracted to be used in the regression algorithm to estimate the changes in the RHC mean pressure (MP) values (e.g., changes in pulmonary artery mean pressure (ΔPAM), and changes in pulmonary capillary wedge mean pressure [ΔPCWP]). The $MP_{BL}$ and $MP_{VI}$ values were extracted from the RHC Mac-Lab computer and used to calculate the target variable (ΔPAM and ΔPCWP). FIG. 6C provides details on the wearable signal processing. First, the R-peaks of the ECG signals were detected, and the SCG signals were segmented into individual heartbeats. Second, $SCG_{BL}$ and $SCG_{VI}$ heartbeats were passed through an outlier removal algorithm (using principal component analysis (PCA) and Gaussian mixture model (GMM)) and were ensemble-averaged to have two average SCG heartbeats per axis (one for BL and one for VI). Third, DTW distances were calculated between the BL and VI heartbeats per axes and used as features (f) in the regression algorithm.

Both systems were time-synchronized before the procedure was started. The PAM and PCWP values for both the baseline (BL) and during vasodilator infusion (VI) were extracted by a HF cardiologist (LK) and later used to calculate the ΔPAM and ΔPCWP by subtracting the mean pressure values during the BL from the mean pressure values during VI respectively.

The $PCWP_{VI}$ value for one subject was not recorded due to a technical issue in the Mac-Lab system and is missing from the analysis. In total, ΔPAM values were available for 20 subjects (15 subjects for the training-testing set and five subjects for the validation set), and ΔPCWP values were available for 19 subjects (14 subjects for the training-testing set and five subjects for the validation set).

The synchronized timestamps were used to extract 20 seconds long wearable signals (ECG and SCG) from both BL and VI states of the protocol when the catheter was at the PA and pulmonary capillary wedge positions. The changes in the wearable signals were analyzed with the ΔPAM and ΔPCWP values and later used in a population regression model with cross-validation. The details of the wearable signal processing, feature extraction, and regression model are given below.

Preprocessing and Noise Reduction: The BL and VI wearable signals were processed (filtering, removal of outliers, and ensemble averaging) separately and later used to calculate the DTW distances between the two states (BL and VI). The DTW distances between different portions of the SCG signals from different axes were used in a regression algorithm to estimate ΔPAM and ΔPCWP with leave-one-subject-out (LOSO) cross-validation on the training-testing set and later validated on the independent validation set.

The raw ECG and SCG signals from the wearable patch were digitally filtered and a fourth SCG signal representing the accelerometermagnitude ($SCG_{Mag}$) was calculated using vector summation of the three SCG axes already obtained ($SCG_{HtoF}$, $SCG_{Lat}$, $SCG_{DV}$). Following the filtering step, the R-peaks of the ECG signals were detected and used to segment the 20-second long signals of the four axes of SCG into individual heartbeats. The SCG heartbeats were cropped to a duration of 500 ms before and after the R-peak that roughly represents most of the relevant diastolic and systolic cardiac events of interest (e.g., rapid inflow, atrial systole, isovolumetric contraction, ventricular ejection, etc.).

Figure 7A:
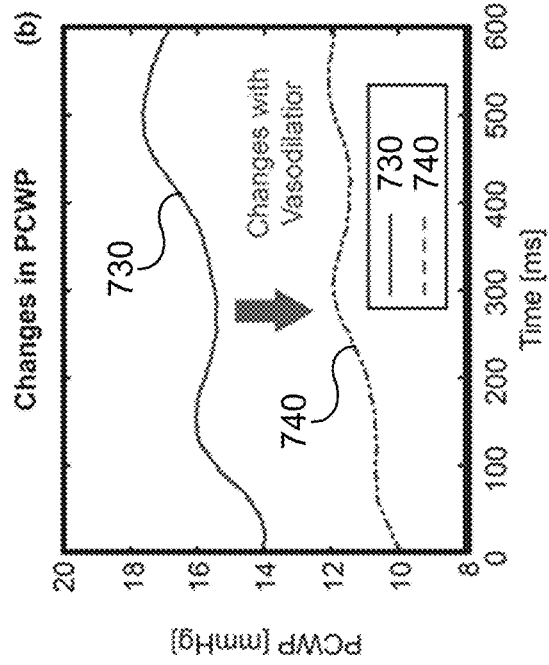
FIG. 7A provides a graph of experimentally measured pulmonary artery (PA) pressure, in accordance with the present disclosure.
Figure 7B:
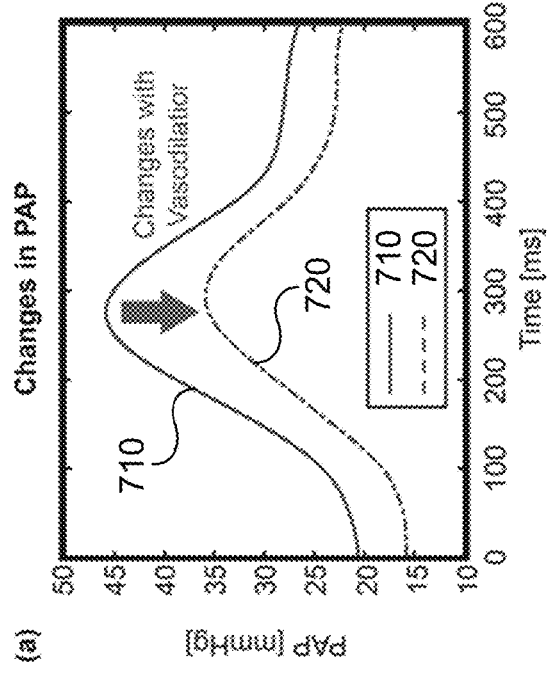
FIG. 7B provides a graph of experimentally measured pulmonary capillary wedge pressure (PCWP), in accordance with the present disclosure.
Figure 7C:
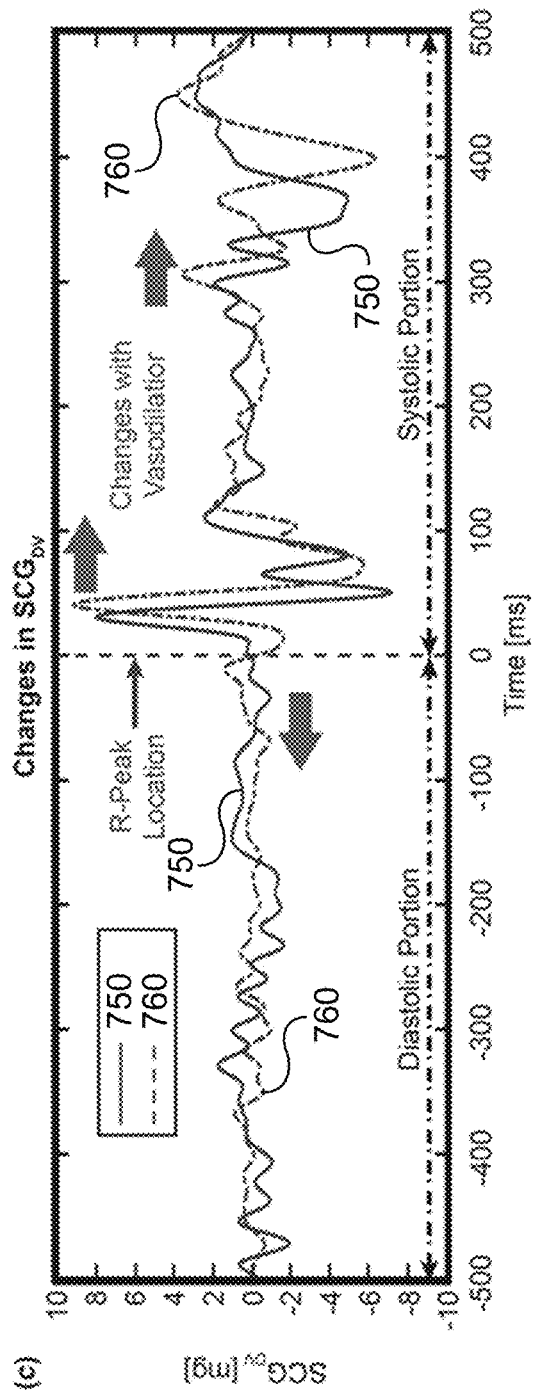
FIG. 7C provides a graph of experimentally measured SCG data, in accordance with the present disclosure.
Figure 8A:
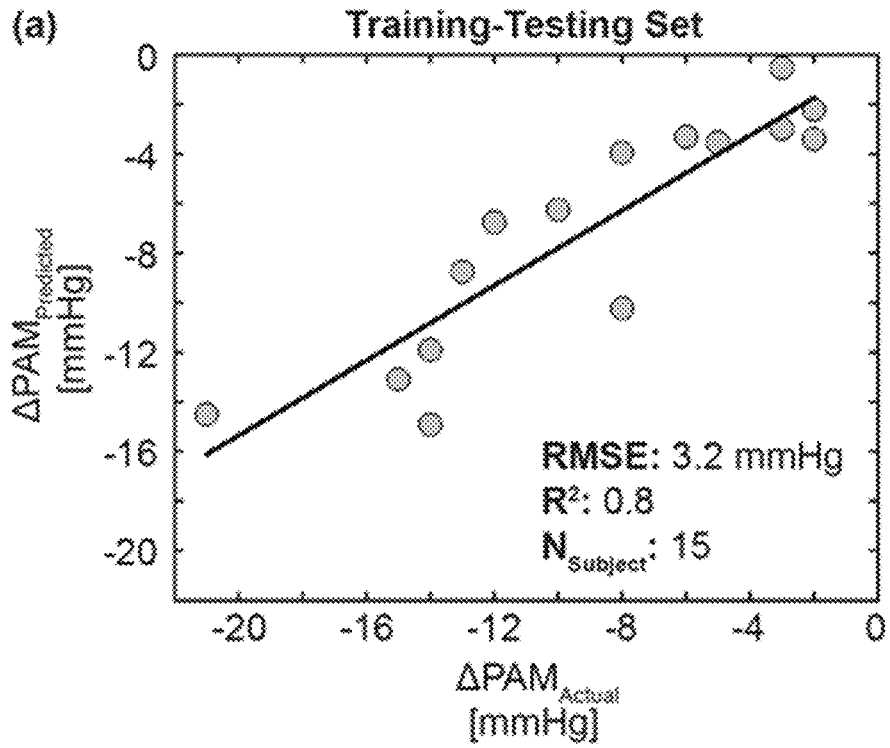
FIG. 8A provides a graph of correlation analysis, in accordance with the present disclosure.
Figure 8B:
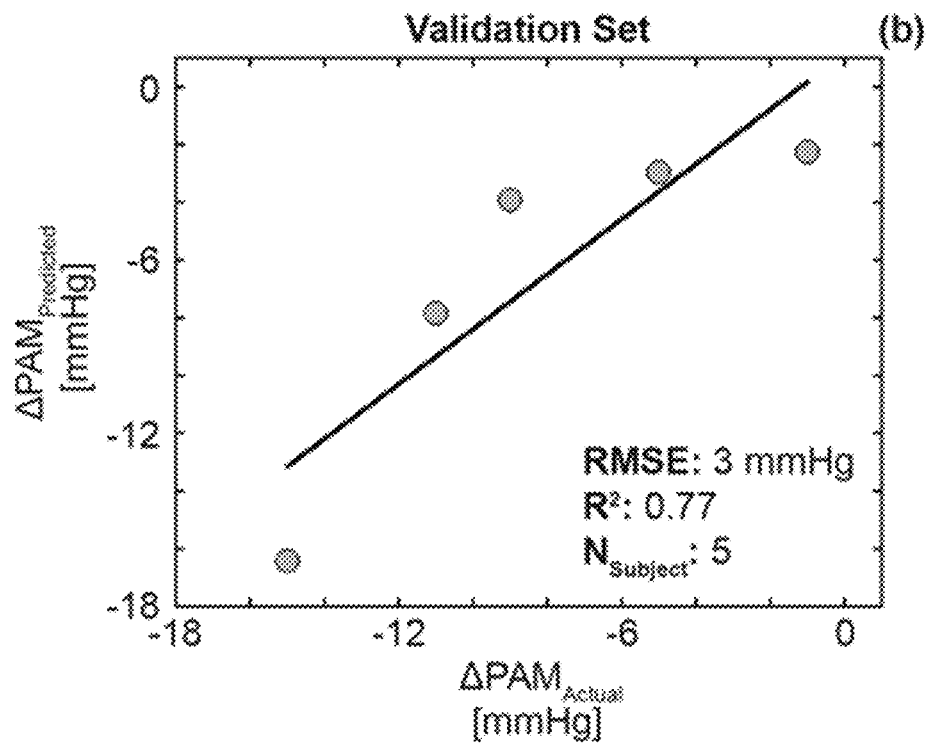
FIG. 8B provides a graph of correlation analysis, in accordance with the present disclosure.
Figure 8C:
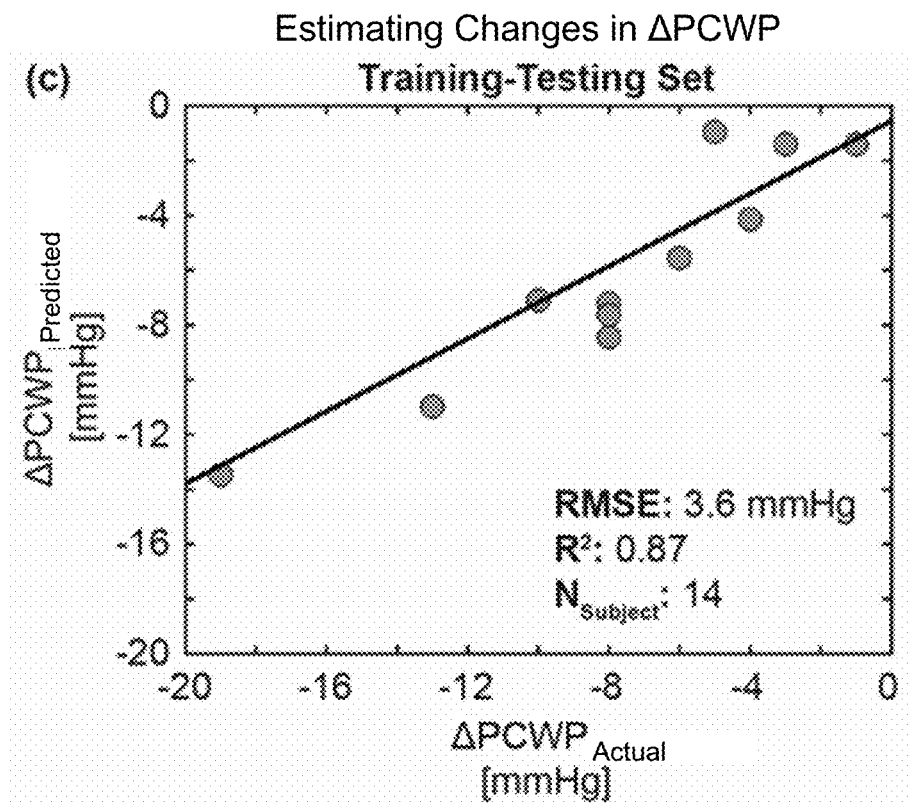
FIG. 8C provides a graph of correlation analysis, in accordance with the present disclosure.
Figure 8D:
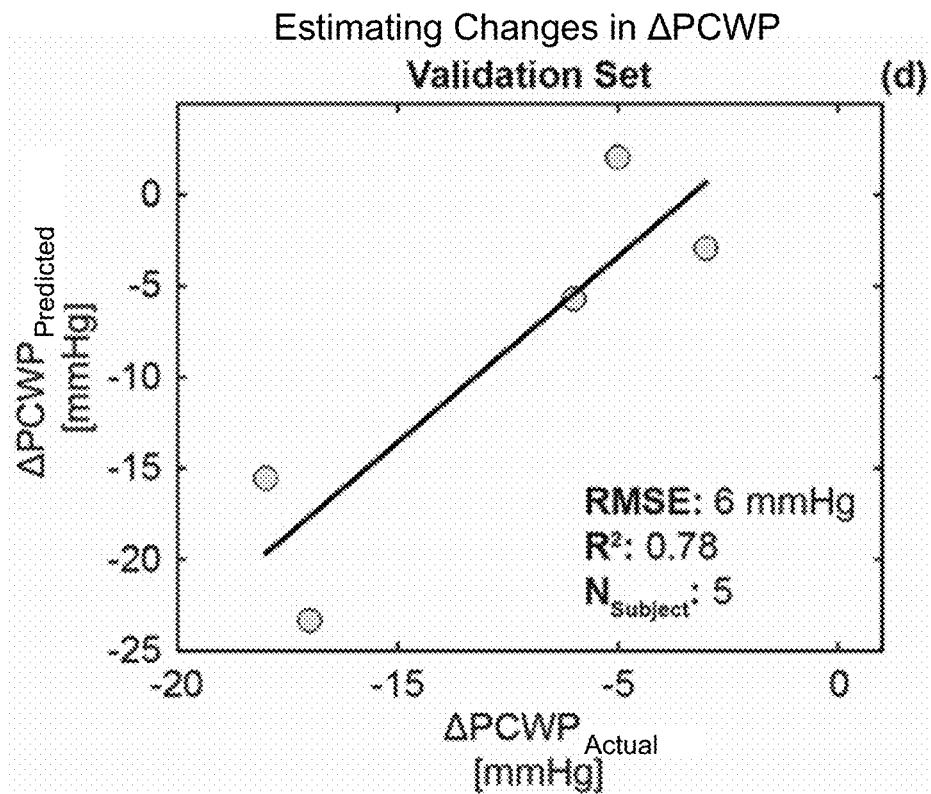
FIG. 8D provides a graph of correlation analysis, in accordance with the present disclosure.

Following the heartbeat segmentation of the wearable SCG signals, the outlier heartbeats from the SCG were removed for the two distributions from the two states (BL and VI) for each axis and each portion (diastolic and systolic) of the SCG signals separately using an automated unsupervised algorithm (details in supplementary materials section below). The actual SCG heartbeats corresponding to the outliers for the distribution were removed and resulted in two separate distributions per axis (SCGBL and SCGVI). The remaining heartbeats were ensemble-averaged to create two ensemble-averaged heartbeats for BL and VI for a particular axis and portion, which were later used to calculate the DTW distances. The ensemble-averaging step reduced the inherent variabilities and remaining noises in the SCG heartbeats. FIG. 7 shows the ensemble-averaged SCGDV heartbeats from the BL and VI states and corresponding PAP and PCWP heartbeats. FIG. 8 provides in FIG. 7A changes in PAP showing PAPBL 710 and PAPVI 720, in FIG. 7B changes in PCWP showing PCWPBL 730 and PCWPVI 740, and in FIG. 7C changes in SCG in the DV direction (SCGDV) showing SCGBL 750 and SCGVI 760 with the infusion of vasodilator for a representative subject, with arrows showing the changes in the respective signals. Time "0" indicates the location of the corresponding ECG R-peak.

Figure 9A:
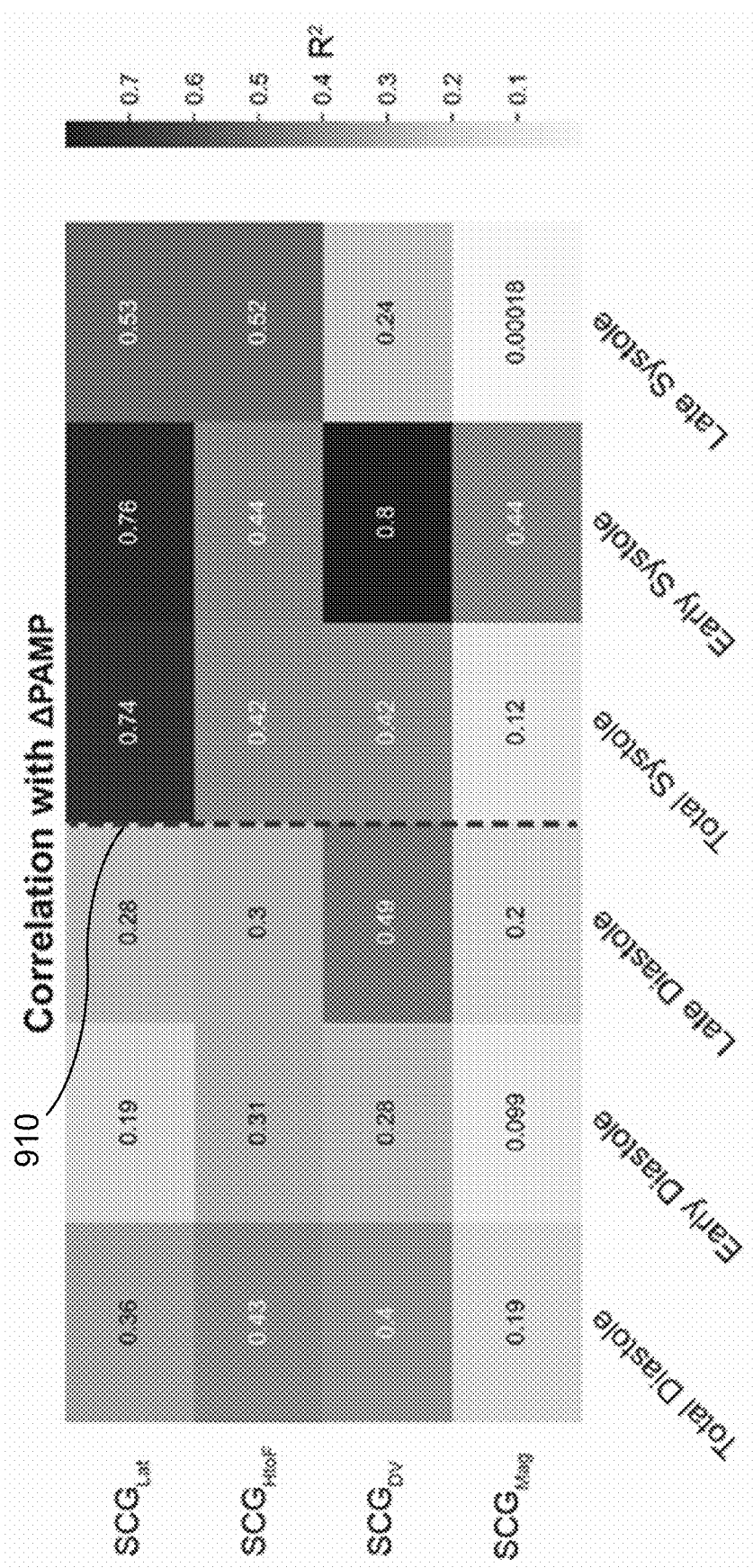
FIG. 9A provides a chart of correlation analyses, in accordance with the present disclosure.
Figure 9B:
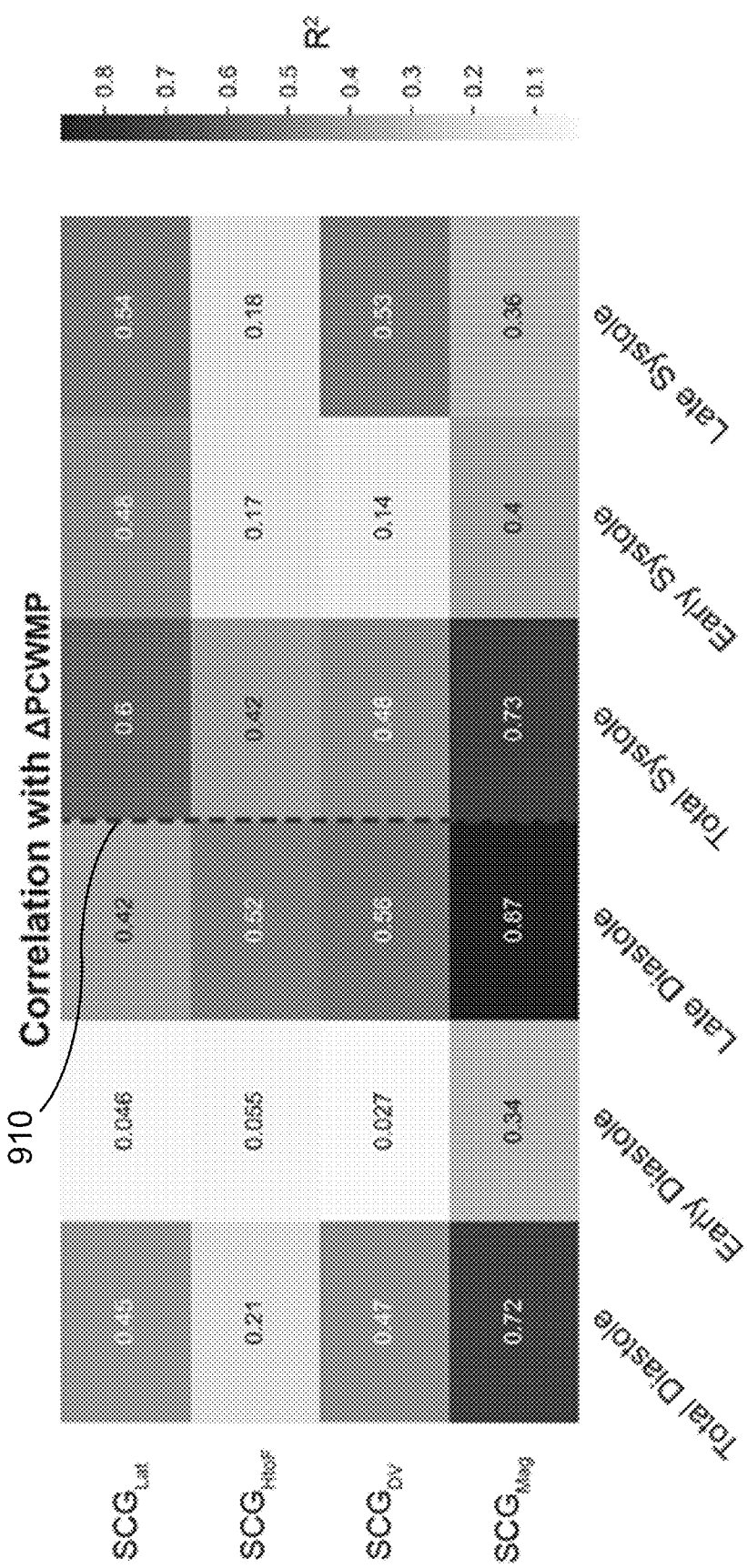
FIG. 9B provides a chart of correlation analyses, in accordance with the present disclosure.

DTW and Feature Extraction: To calculate the changes in SCG from BL to VI, we leveraged DTW and compared the DTW distances from different portions of the SCG heartbeats to the ΔPAM and ΔPCWP with correlation analyses, shown in FIG. 9. FIG. 9 provides correlation analysis of the target variable, in FIG. 9A ΔPAM and in FIG. 9B ΔPCWP, with different DTW distances of corresponding SCG signals for the training-testing set, with the colorbar showing the $R^2$ values and the dotted line 910 indicating the division between ventricular diastole and systole (i.e., R-peak of corresponding ECG). Total Diastole (−500 ms:R-peak), early diastole (−500 ms: −200 ms), late diastole (−200 ms:R-peak), total systole (R-peak: 500 ms), early systole (25 ms: 150 ms), and late systole (200 ms: 500 ms). The DTW is a time-series analysis method to align signals and find similarities between signals. The DTW distances between signals from BL and VI were calculated from different portions of the SCG heartbeats: total diastole (−500 ms:R-peak), early diastole (−500 ms:−200 ms), late diastole (−200 ms:R-peak), total systole (R-peak: 500 ms), early systole (25:150 ms), and late systole (200:500 ms), where negative time represents prior to the R-peak and positive time represents following the R-peak. Early diastole corresponds to the passive ventricular filling, late diastole corresponds to the atrial systole, early systole corresponds to isovolumetric contraction (IVC), and late systole corresponds to the ventricular ejection phase of the cardiac cycle.

The preprocessing and feature extraction process described above were performed in the same way for both the training-testing and validation dataset. Following the feature extraction process, only the data from the training-testing set were used to develop a regression algorithm using LOSO cross-validation. The model's hyperparameters were tuned in this step to maximize the performance (maximize the coefficients of determination, $R^2$, and minimize the RMSE of the developed model on the training-testing set. The resulting trained model was later validated on the independent validation set to showcase the generalizability of the developed models. The details of this step are given in the following section.

D. Regression

Before developing a regression algorithm using the data from the training-testing set, the features (i.e., DTW distances) were compared from the different portions of SCG heartbeats with the target variable, using in a simple correlation analysis (shown in FIG. 9) and the coefficients of determination ($R^2$) was calculated between them to analyze which segments of the SCG are more relevant to track changes in PAM and PCWP. Later, the DTW distances were used as features to build and tune regression algorithms to estimate the changes in PAM and PCWP on the training-testing set and later validated on the independent validation set.

Following the simple correlation analysis, a population level regression model with LOSO cross-validation was performed on the training-testing set to estimate the ΔPAM and ΔPCWP from the DTW distances. Different regression algorithms were explored for this purpose, and, the support vector regression (SVR) model with a linear kernel was chosen as the regression model from our initial analysis.

As the simple correlation analysis between the DTW distances from different portions of the SCG heartbeats and corresponding target variables (ΔPAM and ΔPCWP) for the training-testing set is shown in the FIG. 9, not all the changes from the different portions of the SCG (i.e., DTW distances) are relevant to the changes in the mean pressures (MP). For that reason, a feature selection technique was performed using a sequential forward selection (SFS) algorithm to select the top five features as the estimating variables in the regression model.

Using a LOSO cross-validation for 15 subjects in the training-testing set, we trained a linear SVR regressor on the selected (using SFS method) DTW distances from 14 subjects, leaving one subject out at each fold. The target variables (ΔPAM and ΔPCWP) were predicted for the left-out subject, repeating this 14 more times with a different subject excluded each time. As a result, we obtained predictions for all 15 subjects in the training-testing set. This cross-validation method was used to develop a global regression model with optimized hyperparameters on the data in the training-testing set only. For the validation of the global model, the regression model (with the optimized hyperparameters) was trained on the whole training-testing set (data from 15 subjects) and tested on the separate validation set (data from five subjects). As a result, all the target variables were predicted, from all 20 subjects.

Two figures of merit were used to evaluate the regression model and approach. First, the RMSE was calculated between the estimated target variable ($\Delta MP_{Pred}$) and the ground truth target variable from the Mac-Lab system ($\Delta MP_{Act}$). Second, a simple correlation analysis (Pearson) was performed between the true values and the predictions of ΔMP to get the statistical significance of prediction, and the $R^2$ between the true and predicted values was calculated. In this work, p-values below 0.05 were considered to be statistically significant. Both the RMSE and $R^2$ were calculated for the training-testing set and the validation set separately.

Results

Patient demographics and clinical characteristics are detailed in TABLE V, and RHC characteristics are provided in TABLE VI.

TABLE V

Subject Demographics and Characteristics

|  | All Subjects (n = 20) | HFrEF Subjects (n = 15) | HFpEF (n = 5) | p-Value |
|---|---|---|---|---|
| Age, years | 54.6 ± 13.2 | 52.7 ± 12.2 | 63.4 ± 13.2 | 0.07 |
| Sex |  |  |  |  |
| Male | 16 (80%) | 12 (80%) | 4 (80%) | . . . |
| Female | 4 (20%) | 3 (20%) | 1 (20%) |  |
| Height, cm | 175.3 ± 9.9 | 174.4 ± 10.2 | 177.8 ± 9.7 | 0.46 |
| Weight, kg | 94.2 ± 19.4 | 94.4 ± 21.2 | 93.7 ± 14.7 | 0.93 |
| BMI, kg/m² | 30.6 ± 5.9 | 31 ± 6.5 | 29.6 ± 3.8 | 0.86 |
| Ejection fraction, % | 31.8 ± 19.5 | 21.8 ± 7.5 | 61.7 ± 10.9 | 0.001 |

TABLE V-continued

Subject Demographics and Characteristics

|  | All Subjects (n = 20) | HFrEF Subjects (n = 15) | HFpEF (n = 5) | p-Value |
|---|---|---|---|---|
| NYHA class |  |  |  |  |
| I | 1 (5%) | 0 (0%) | 1 (20%) |  |
| II | 3 (15%) | 3 (20%) | 0 (0%) |  |
| III | 11 (55%) | 7 (47%) | 4 (80%) |  |
| IV | 5 (25%) | 5 (33%) | 0 (0%) |  |
| Systolic blood pressure, mmHg | 114 ± 13 | 109 ± 11 | 126 ± 11 | 0.008 |
| Diastolic blood pressure, mmHg | 67 ± 11 | 68 ± 9 | 64 ± 15 | 0.76 |

Values shown are mean±SD or n (% of the population) unless otherwise indicated. Statistical significance between HFrEF and HFpEF subjects in values, where applicable, was evaluated using a Mann-Whitney U test.; BMI, Body Mass Index; NYHA, New York Heart Association.

TABLE VI

Right Heart Catheterization Responses

|  | All Subjects (n = 20) | HFrEF Subjects (n = 15) | HFpEF (n = 5) | p-Value |
|---|---|---|---|---|
| PA mean pressure BL, mmHg | 34.7 ± 6 | 36 ± 6 | 30.8 ± 4.8 | 0.12 |
| PA mean pressure VI, mmHg | 25.8 ± 5.2 | 26.4 ± 5 | 24.2 ± 6.2 | 0.36 |
| Change in PA mean pressure, mmHg | −8.9 ± 5.5 | −9.6 ± 5.5 | −6.6 ± 5.3 | 0.29 |
| PCWP BL, mmHg | 22.4 ± 5.2 | 23.9 ± 5 | 17.8 ± 2.5 | 0.012 |
| PCWP VI, mmHg | 14.5 ± 5.2 | 15.3 ± 5.2 | 12.2 ± 5 | 0.4 |
| Change in PCWP, mmHg | −8.2 ± 6.8 | −9 ± 7.4 | −5.6 ± 4.2 | 0.38 |
| Right atrial mean pressure BL, mmHg | 10.9 ± 6.1 | 12 ± 6.4 | 7.6 ± 4 | 0.2 |
| Right ventricular end-diastolic pressure BL, mmHg | 13.3 ± 6.6 | 14.6 ± 6.6 | 8.25 ± 3.3 | 0.067 |
| Heart rate, BL, beats per minute | 75.8 ± 16.8 | 79.9 ± 17.1 | 63.2 ± 7.9 | 0.09 |
| Heart rate, VI, beats per minute | 77 ± 15.9 | 80.1 ± 16.9 | 67.8 ± 8 | 0.14 |
| Stroke volume BL, mL/beat | 58.5 ± 25 | 50.5 ± 19.6 | 82.3 ± 26.3 | 0.045 |
| Fick cardiac output BL, L/min | 4.3 ± 1.3 | 4 ± 1.1 | 5.1 ± 1.7 | 0.17 |
| Thermodilution cardiac output BL, L/min | 4.1 ± 1.3 | 4 ± 0.9 | 5.2 ± 1.7 | 0.067 |
| CI BL, L/min/m² | 1.9 ± 0.5 | 1.8 ± 0.3 | 2.4 ± 0.8 | 0.097 |

Values shown are mean ± SD unless otherwise indicated.
Statistical significance between HFrEF and HFpEF subjects in values, where applicable, was evaluated using a Mann-Whitney U test.;
BL, Baseline Values;
VI, Vasodilator Infused Values.
There were 15 patients with HFrEF and 5 with HFpEF; four patients were women, and the mean age was 54.2 ± 13.2 years. The mean weight was 94.2 ± 19.4 kg, height 175.3 ± 9.9 cm, and the mean ejection fraction (EF) was 32 ± 19.5).

Values shown are mean±SD unless otherwise indicated. Statistical significance between HFrEF and HFpEF subjects in values, where applicable, was evaluated using a Mann-Whitney U test.; BL, Baseline Values; VI, Vasodilator Infused Values.

There were 15 patients with HFrEF and 5 with HFpEF; four patients were women, and the mean age was 54.6±13.2 years. The mean weight was 94.2±19.4 kg, height 175.3±9.9 cm, and the mean ejection fraction (EF) was 32±19.5).

Figure 10A:
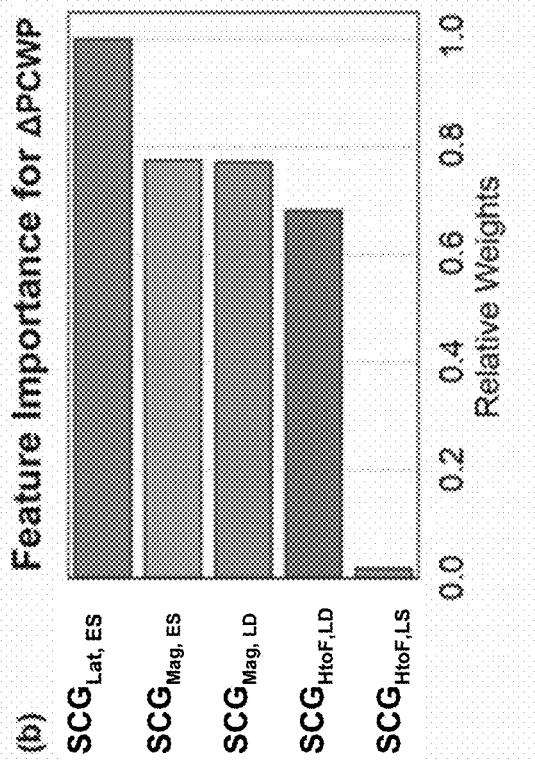
FIG. 10A provides a graph of relative weights of algorithm features, in accordance with the present disclosure.
Figure 10B:
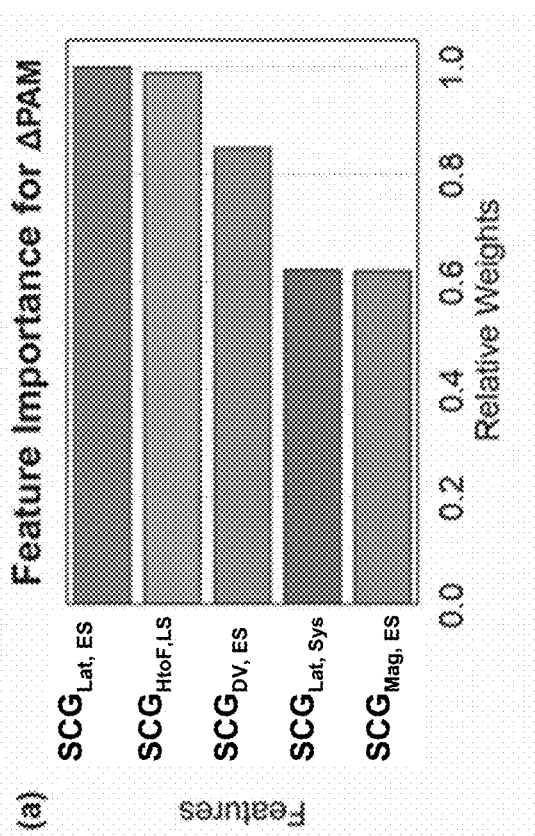
FIG. 10B provides a graph of relative weights of algorithm features, in accordance with the present disclosure.

With vasodilator infusion, the PAM and PCWP decreased by 8.9±5.5 mmHg and 8±6.3 mmHg, respectively, from the corresponding BL values. FIG. 7 shows the changes in PAP and PCWP signals and the changes in $SCG_{DV}$ with vasodilator infusion for one representative subject. Note that all the signals shown in the figure are synchronized with the corresponding R-peak. The overall mean of the PAP and PCWP signals decreased with vasodilator infusion, whereas the systolic portion of the $SCG_{DV}$ signal shifted later with respect to the ECG R-peak following vasodilator infusion. FIG. 9 shows the correlation analysis (i.e., $R^2$ values) between the DTW distances (changes in SCG signals with vasodilator) from different portions and axes of the SCG signals with changes in pulmonary artery mean pressure (ΔPAM) and changes in pulmonary capillary wedge mean pressure (ΔPCWP), whereas FIG. 10 shows the selected five DTW distances using the feature selection technique mentioned in the method section, and their relative importance (weights) in the regression model for the training-testing set. FIG. 10 provides relative feature importance ranking (i.e., relative weights) of the features in the regression algorithm for ΔPAM (FIG. 10A) and ΔPCWP (FIG. 10B) on the training-testing set. Dias: Total Diastole, ED: Early Diastole, LD: Late Diastole, Sys: Systole, ES: Early Systole, and LS: Late Systole. Time-length for the segments is explained in the FIG. 9.

FIG. 8 shows the correlation analysis between the actual (measured) and the estimated ΔPAM and ΔPCWP values for both the training-testing and validation set. FIG. 8 provides correlation analysis for ΔPAM predicted vs. ΔPAM actual on the training-testing set (FIG. 8A) and validation set (FIG. 8B). Correlation analysis for ΔPCWP predicted vs. ΔPCWP actual on the training-testing set (FIG. 8C) and validation set (FIG. 8D). The correlation results show an RMSE of 3.2 mmHg and an $R^2$ of 0.8 for the training-testing set and an RMSE of 3 mmHg and an $R^2$ of 0.77 for the validation set for ΔPAM, and an RMSE of 3.6 mmHg and an $R^2$ of 0.87 for the training-testing set and an RMSE of 6 mmHg and an $R^2$ of 0.78 for the validation set for ΔPCWP.

A. Supplemental Materials

Training-Testing and Validation Set Separation: The dataset was separated randomly into two groups of 15 HF patients for a training-testing set and five HF patients for a separate independent validation set, with a 75:25 ratio respectively. The only constraint used to separate the dataset was to keep the same ratio of HF with reduced ejection fraction (HFrEF) and HF with preserved ejection fraction (HFpEF) subjects for both the training-testing and validation set. The random separation resulted in four HFpEF subjects in the training-testing set and one HFpEF subject in the validation set.

Filtering and Heartbeat Segmentation: The raw ECG and SCG signals from the wearable patch were digitally filtered (cut-off frequencies: 0.5-40.0 Hz for the ECG and 1-40 Hz for the SCG signals) to remove out-of-band noise. These cut-off frequencies were employed to remove out-of-band noise without distorting the shape of the signals. After the filtering step, a fourth SCG signal representing the accelerometermagnitude ($SCG_{Mag}$) was computed using vector summation of the three SCG axes already obtained ($SCG_{HtoF}$, $SCG_{Lat}$, $SCG_{DV}$).

The ECG signal (in the 20-second frame) was amplitude-normalized and the R-peaks of the ECG signal were detected using the Pan Tompkins method. The SCG signals (four axes of SCG) were segmented into individual heartbeats using the R-peaks of the ECG signal. Each heartbeat was cropped to a duration of 500 ms before and after the R-peak. The 500 ms SCG frame before the R peak roughly represents the ventricular diastolic phase, and the 500 ms SCG frame after the R peak roughly represents the ventricular systolic phase of the cardiac cycle. The duration of 500 ms before and after the R-peak was chosen as most of the relevant diastolic and systolic cardiac events of interests (e.g., rapid inflow, atrial systole, isovolumetric contraction, ventricular ejection, etc.) occur within this time frame, with respect to the corresponding R-peak of ECG. A constant time window was chosen to crop the ECG and SCG signals to have a repeatable and globalized feature extraction process.

SCG Outlier Heartbeats Removal: Following the heartbeat segmentation of the wearable SCG signals, the outlier heartbeats were removed from the SCG for the two distribution from the two states (baseline, BL and vasodilator-infused, VI) for each axis and each portion (diastolic and systolic) of the SCG signals separately. For outlier removal from a particular distribution, the dimension of the 500 sample long SCG heartbeats (for 500 ms long frame with a 1 kHz sampling frequency) was reduced into three dimensions by using principal component analysis (PCA) and taking the first three principal components (PC). This low-level representation of the SCG heartbeats was used in a Gaussian-mixture model (GMM) to determine the probability that each sample belongs to a particular distribution (BL or VI) for a particular portion and a particular axis of SCG. For a particular distribution, the points with the lowest 20% probability were detected as the outlier for the distribution. The cut-off of 20% was chosen based on the initial analysis, with 10%, 20%, and 30% beats removed as outliers. The number of principal components (e.g., three in this case) to create the GMM for a particular distribution was based on the analysis on the percentage of variance explained by the number of PCs and the overall estimation accuracy. As most of the power in the SCG signal stays in the systolic portion of the signal, it might end up dominating the outlier removal in the diastolic portion of the signal. For that reason, the outlier removal was performed separately for the diastolic and systolic portions of the SCG.

Correlation Analysis between SCG DTW Distances with ΔPAM and ΔPCWP: FIG. 9 shows the $R^2$ values between the DTW distances from different portions and axes of the SCG signals with ΔPAM and ΔPCWP for the training-testing set. In the case of ΔPAM, the changes in SCG during the early systole (isovolumetric contraction, IVC, period) provided the most relevant information related to changes in the PAM, with changes in SCG in the DV direction ($SCG_{DV}$) during the IVC period showing the highest $R^2$ of 0.8 with ΔPAM. In the case of ΔPCWP, the changes in the SCG during the late diastole (atrial systole) phase provided the most relevant information related to changes in PCWP, with changes in SCG magnitude signal ($SCG_{Mag}$) during the late diastole period (atrial systole) showing the highest $R^2$ of 0.87 with ΔPCWP. Overall, the figure is showing that ΔPAM is more related to the changes in the systolic portion (IVC period more precisely) of the SCG signal, whereas ΔPCWP is more related to the changes in the late ventricular diastole (i.e., atrial systole) portion of the SCG. It might be explained with physiological rationale, as the PA is directly connected to the right ventricle, the ventricular systole (contraction) phase is dominating the changes in PAM. On the other hand, the pulmonary capillaries are connected to the left atrium and showing more relation with atrial systole. These preliminary results can be verified with simultaneous imaging modalities in a large population study with diversified subjects with various cardiovascular conditions.

Relative Feature Importance: FIG. 10 shows the relative weights of the features in the support vector regression with linear kernel for the estimation of ΔPAM and ΔPCWP in the training-testing set, with the top feature related to both ΔPAM and ΔPCWP being the change $SCG_{Lat}$ during the IVC period. Similar to the results obtained from the individual correlation analysis (in FIG. 9) between the target variables (ΔPAM and ΔPCWP) with the DTW distances, all the top five features for the ΔPAM are from the systolic portion of the SCG. In the case of ΔPCWP, three of the top five are from the systolic portion of the SCG, and two are from the diastolic portion of the SCG. Both FIGS. 10 and 11 show the importance of the diastolic portion of the SCG in estimating ΔPCWP. Most of the SCG research works are concentrated on the systolic portion of the signal. These results suggest that the diastolic portion of the SCG signal also has the potential to provide relevant information regarding pulmonary congestion.

Discussion

This example shows that changes in SCG can track acute changes in PAM and PCWP due to systemic vasodilator infusion in patients with HF. SCG signals obtained using a wearable patch can thus track changes in hemodynamic congestion. These results provide for tracking changes in hemodynamics in patients with HF in their daily life and activities via wearable sensors.

Two findings in this example were the individual feature (DTW distances) correlation and feature importance ranking corresponding to the changes in PAM and PCWP due to systemic vasodilator infusion. The results from this example show that the changes in SCG during the ventricular systolic portion of the cardiac cycle (more specifically IVC period) provide salient information about the changes in PAM, whereas the changes in the SCG signals during ventricular systole and atrial systole (active ventricular diastolic period) provided the most pertinent information regarding changes in PCWP. With vasodilator infusion, the PAM and PCWP decrease as does preload, and IVC time interval (i.e., PEP) is inversely correlated with preload. For that reason, with a decrease in preload, we observe an increase in PEP (as shown in FIG. 7), which is as expected. These scientific findings disclose a way toward elucidating the origin of the SCG signal itself, and disclose the use of these signals to extract physiologically meaningful information beyond vital signs and cardiac timing intervals. These results also show the importance of the ventricular diastolic portion of the SCG signals, which is often neglected in most research works focused on SCG. Imaging modalities can be incorporated to understand how the changes in SCG are related to underlying physiological changes due to physiological or pharmacological perturbation.

Another finding from this example is the use of simple linear models (linear SVR) rather than complex non-linear models to estimate the changes in hemodynamic congestion. Simple linear models can provide more insights into the model and corresponding features used to build the model compared to the complex non-linear models, which are sometimes "black box" in nature. As there was a small number of subjects for this study, using a simpler regression model provided a better understanding of the important features (segments and axes of the SCG) that are relevant to acute changes in hemodynamic congestion, and increased confidence in the generalizability of the methods. These methods make the models more physiologically insightful and interpretable.

Another finding of this study was the use of noise reduction and outlier removal that improved the overall accuracy of estimation significantly. The results from the analysis demonstrated that having 20-30 seconds of high-quality wearable ECG and SCG recordings is sufficient to track changes in hemodynamic congestion.

The wearable patch of this example demonstrated that cardiopulmonary fitness parameters (i.e., instantaneous oxygen uptake and clinical state of patients) can be tracked from both patients with HF in a controlled clinical setting (cardiopulmonary exercise test) and healthy subjects in an uncontrolled daily life setting. The method of tracking changes in hemodynamic congestion using SCG described in this example can be incorporated with the methods of tracking cardiopulmonary parameters using SCG in this disclosure.

In this example, we have estimated the changes in PA mean pressure and PCWP in patients with HF due to vasodilator infusion with the changes in simultaneously recorded SCG signal. We have developed a global regression model for the estimation of ΔPAM and ΔPCWP using machine learning algorithms validated with leave-one-subject-out cross-validation. We have demonstrated that tracking changes in SCG can track changes in the subclinical congestion, which has the potential to be used for remote home management for patients with HF. Overall, this work demonstrates the capability of an unobtrusive wearable patch to track hemodynamic congestion.

Example 2

In this Example, we present a wearable, inexpensive, minimally obtrusive system to remotely monitor HF patients using wearable SCG. The SCG signal captures the vibrations of the chest wall in response to the cardiac ejection of blood and the movement of the heart. The use of SCG signals was investigated to classify the clinical status of HF patients in a resting state. Specifically, in this Example, it is demonstrated the accurate classification of the clinical status of HF patients in a resting state. This classification provides an indication of elevated filling pressures and decreased CI as the clinical status of the patients are determined using PCWP and CI. The ability to detect elevated PCWP provides valuable information to healthcare providers similar or better than implantable devices that measure PA pressures as PCWP is a better indicator of left sided filling pressures. All the data in this Example were collected in the cardiac catheterization laboratory to acquire both SCG signals and hemodynamic parameters while patients were undergoing standard of care RHC. Note that although all the data collected for this Example were from measurements in the hospital, we expect that these models can generalize to in-home settings as they only need data from the non-invasive wearable patch to perform clinical status estimation.

Results

A. Clinical Status of Patients with HF was Accurately Classified Using SCG Features Experiments were conducted to assess the discriminatory ability of SCG features in HF clinical status, which is determined clinically from elevated filling pressures and low CI. To build a machine learning model, a binary classification task was defined where the input was a set of 83 extracted features, and the output represented the hemodynamic congestion status of the patient as decompensated (PCWP≥20 mmHg and CI≤2.2 L/min/m$^2$) or compensated. For this task, all the model development was performed on data from 50 patients (52 recordings). This data hereafter is referred to as the training set. After we built the classification model on the training set, we used unseen data from 13 other patients to quantify the generalization performance of the developed classification model. We refer to this data as the validation set. TABLES VII and VIII provide demographic information on the subjects in the training and validation sets, respectively.

TABLE VII

Demographic Information of Subjects in Training Set.

|  | Gender | | NYHA Class | | |
| --- | --- | --- | --- | --- | --- |
|  | Male | Female | II | III-IV | Overall |
| # Patients | 33 | 17 | 14 | 36 | 50 |
| # Comp. Recordings | 16 | 13 | 9 | 20 | 29 |
| # Decomp. Recordings | 18 | 5 | 5 | 18 | 23 |
| Age ($\mu \pm \sigma$) | 57.4 ± 13.6 | 52.9 ± 14.5 | 57.0 ± 14.6 | 55.4 ± 13.9 | 55.8 ± 13.9 |
| Height ($\mu \pm \sigma$, in cm) | 176.5 ± 8.2 | 165.1 ± 6.8 | 172.2 ± 7.7 | 172.8 ± 10.1 | 172.6 ± 9.4 |
| BMI ($\mu \pm \sigma$, in kg/m$^2$) | 30.1 ± 5.4 | 27.1 ± 7.4 | 29.7 ± 6.8 | 28.8 ± 6.1 | 29.0 ± 6.3 |

TABLE VIII

Demographic Information of Subjects in Validation Set.

|  | Gender | | NYHA Class | | |
| --- | --- | --- | --- | --- | --- |
|  | Male | Female | II | III-IV | Overall |
| # Patients | 8 | 5 | 4 | 9 | 13 |
| # Comp. Recordings | 2 | 1 | 0 | 3 | 3 |
| # Decomp. Recordings | 6 | 4 | 4 | 6 | 10 |
| Age ($\mu \pm \sigma$) | 54.1 ± 10.9 | 52.8 ± 20.7 | 60.7 ± 8.2 | 50.4 ± 16.0 | 53.6 ± 14.6 |
| Height ($\mu \pm \sigma$, in cm) | 176.8 ± 9.5 | 161.6 ± 7.7 | 170.2 ± 11.5 | 171.3 ± 12.2 | 171.0 ± 11.5 |
| BMI ($\mu \pm \sigma$, in kg/m$^2$) | 31.2 ± 7.1 | 33.6 ± 13.7 | 26.7 ± 4.5 | 34.6 ± 10.6 | 32.2 ± 9.7 |

Figure 13A:
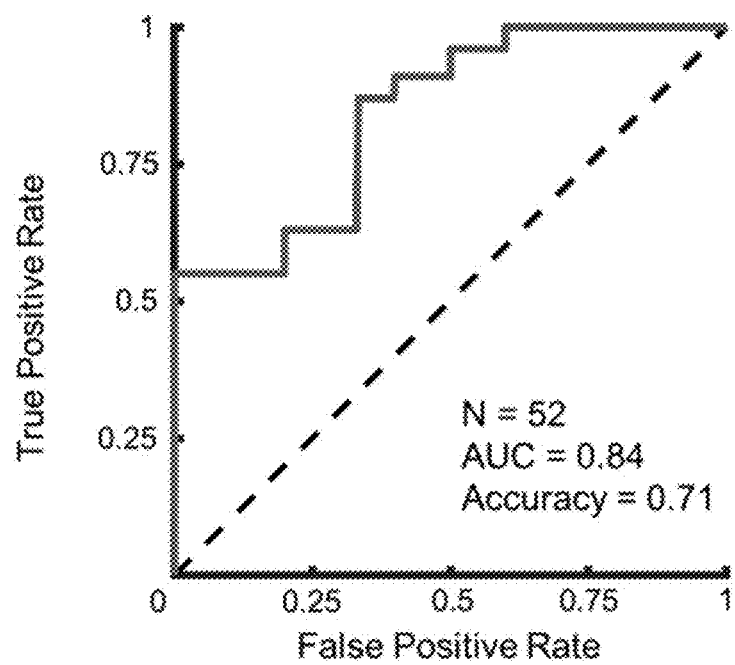
FIG. 13A provides a receiver operating characteristics (ROC) curve for the best classifier using the downselected feature set on the training set, in accordance with the present disclosure.

For the classification model, support vector machines (SVM) were employed for this task. With kernels, SVM can model non-linear relationships between the input, SCG features, and the output, clinical status. In this work, polynomial and rbf kernels were considered to capture possible non-linear relation. To evaluate the performance of the classifiers, five-fold cross validation was performed to compute classification accuracy and AUC on the training set. In each cross-validation split, training and validation data consisted of different subjects, which allow cross-validation performance to be reflective of generalization performance on the unseen new patient data. The results of the experiments are summarized in TABLE IX and FIGS. 13A-B. The first three columns of TABLE IX summarize the results classifying HF clinical status based on the full set of features (82 SCG features). The last column shows the results using subsets of the feature set. The optimal classifier's, using subsets of the extracted features, receiver operating characteristics (ROC) curve is shown in FIG. 13A.

TABLE IX

Classification Performance for Classifiers Performing five-fold Cross Validation on Training Set.

|  | Linear Support Vector Machine (SVM) | Polynomial SVM | RBF SVM | Linear SVM with Feature Selection |
| --- | --- | --- | --- | --- |
| Accuracy | 0.63 | 0.62 | 0.56 | 0.71 |
| AUC | 0.77 | 0.78 | 0.77 | 0.84 |

In this Example, since more features are extracted (83 features) than the number of data points (52 recordings from 50 patients), forward sequential feature selection (SFS) was employed to improve the generalization performance of the classifier. From TABLE IX, it can be seen that using SFS improves the performance of the classifier. Additionally, SFS is informative in identifying which features are useful in performing the task, which in turn provides insights into which aspects of the SCG signal are informative. To employ SFS in five-fold cross validation, nested cross validation was performed. The outer cross-validation loop is used for intermediary evaluation of model performance and the inner cross-validation loop is used for model selection (i.e., SFS and hyperparameter optimization using grid search).

Figure 13B:
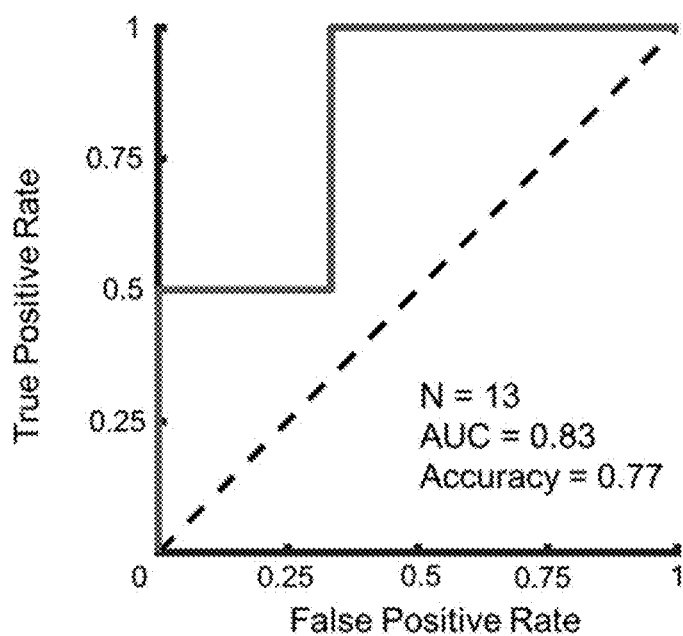
FIG. 13B provides an ROC curve for the model learned on the training set and evaluated on the unseen validation set, in accordance with the present disclosure.

To further quantify the generalization performance of the classification framework, performance metrics were computed on the validation set. Using the entire training set, a new classifier is trained and tested on the validation set. Even though the training set and the validation set class distributions are considerably different, a very similar performance on the unseen validation set as can be seen in FIG. 13B.

B. Informative SCG Features for Assessing Hemodynamic Congestion Include Characteristics from the Lateral Axis and the Diastolic Portion of the Recording The classification models learned in this Example depend on SCG features, and provide insight into SCG signal characteristics relevant to hemodynamic assessment in HF. Since SCG signals are not well understood as compared to other more commonly measured cardiovascular signals—e.g., ECG, photoplethysmogram (PPG), and impedance cardiogram (ICG) signals—this dataset provides an opportunity to advance the knowledge of SCG signal characteristics relevant to assessing congestion status in patients with HF. In this Example, SCG features were identified that are useful in discriminating the clinical status of HF patients. These features are extracted from SCG beats which are processed from the SCG signals. Details about the processing are provided in the Materials and Methods section. The key scientific question addressed is how to best use the collection of SCG beats in a recording to extract discriminative and predictive information. There are three types of features that are examined here, based on the foundational prior work in SCG signal analysis in patients with HF: (1) ensemble averaged beat features from the diastolic and systolic time intervals of the signal; (2) variability features across multiple beats; and (3) frequency domain features.

Ensemble Averaged Beat Features: Some relevant properties of a recording, such as the clinical status and mean filling pressures, do not change substantially from one beat to the next. These properties can be captured from an ensemble averaged beat. The following features were computed from the ensemble averaged beat: square root of the power of the signal (srPower); and delay between R-peak and minimum amplitude (delayMinAmp).

Figure 14A:
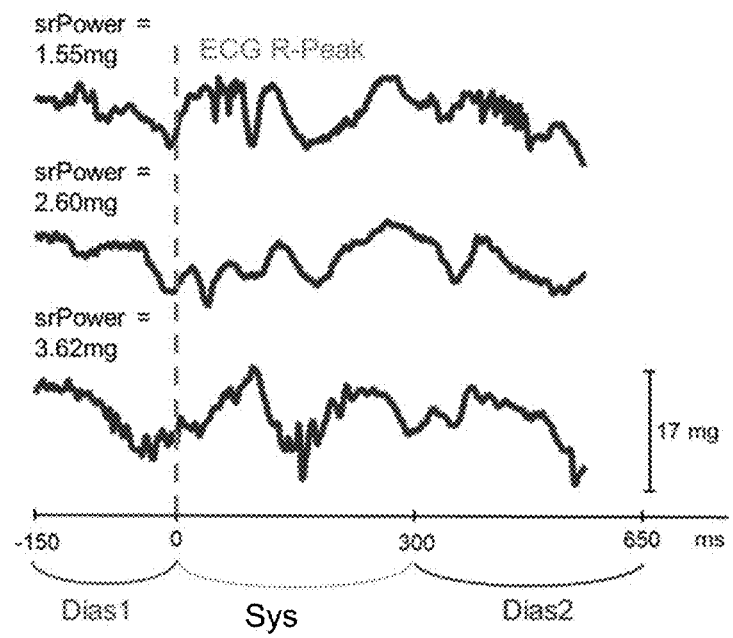
FIG. 14A provides three example beats from one decompensated subject along with base feature (srPower) calculations, in accordance with the present disclosure.

These feature choices are motivated by extensive prior work, which suggests that these measures are correlated with some key cardiac events such as the timing of aortic valve opening, and important event within the cardiac cycle. For a given beat, these features can be computed over different physiologically defined time intervals corresponding to the phases of systole and diastole, which can be indexed based on the ECG signal by defining the location of the ECG R-peak as time zero. Three intervals were defined as illustrated in FIG. 14A (decompensated signal) and FIG. 14B (compensated signal): ventricular diastolic 1 (dias1, from −150 ms to 0 ms); systolic (sys, from 0 ms to 300 ms); and ventricular diastolic 2 (dias2, from 300 ms to 650 ms).

Conventional approaches to SCG analysis focus only on the systolic timing interval; however, since given the interest in finding relationships between the SCG signal and filling characteristics (i.e., PCWP pressure), these typically-omitted intervals were included in the analysis. From each interval, six base level features per channel were obtained by computing the two features. The base level features can be computed for individually segmented beats as well as the ensemble averaged beat.

Figure 14B:
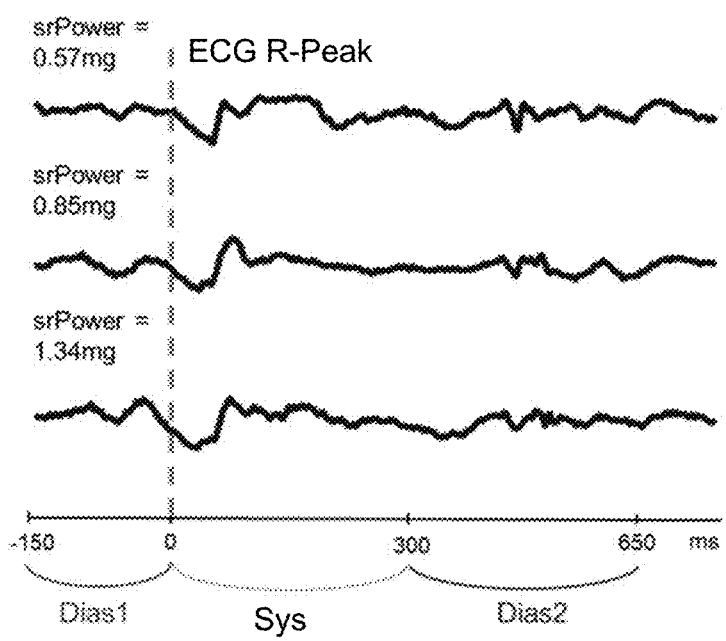
FIG. 14B provides three example beats from one compensated subject along with base feature (srPower) calculations, in accordance with the present disclosure.

Variability Features: In addition to these features from ensemble averaged beats, other features that we examined focus specifically on the variability of the signal in a collection of beats. An HF patient with hemodynamic congestion (decompensated) is hypothesized to have greater variability in the SCG signal than a compensated patient, since the heart and vasculature are operating at a highly sub-optimal state and thus cannot consistently produce beats with similar strength and timing characteristics. Capturing this variability would thus be important because it may signal a sub-optimal clinical state for the cardiovascular system. Specifically, from each individual beat, the base level features are extracted. Then the standard deviation of the feature is computed using the collection of feature values from each beat. An example variability in a feature is shown in FIGS. 14A-B.

The descriptive statistics, such as standard deviation, provide a fixed feature representation across the different length recordings (which will have different numbers of beats). Since standard deviation is computed on each one of the six base level features, six statistical features were computed from the collection of beats.

Frequency Domain Features: The third set of features examined are frequency domain features. In FIGS. 15A-C, normalized PSD of a randomly selected compensated and decompensated recording are visualized. In these visualizations, it can be seen that frequency characteristics around 200-250 Hz and 0-50 Hz are different for decompensated and compensated recordings. Hence, from an SCG recording, two frequency domain features are extracted: ratio of the signal power between 205-250 Hz; and 5-40 Hz and ratio of the signal power between 0-5 Hz to 5-40 Hz.

Figures 16A, 16B, 16C:
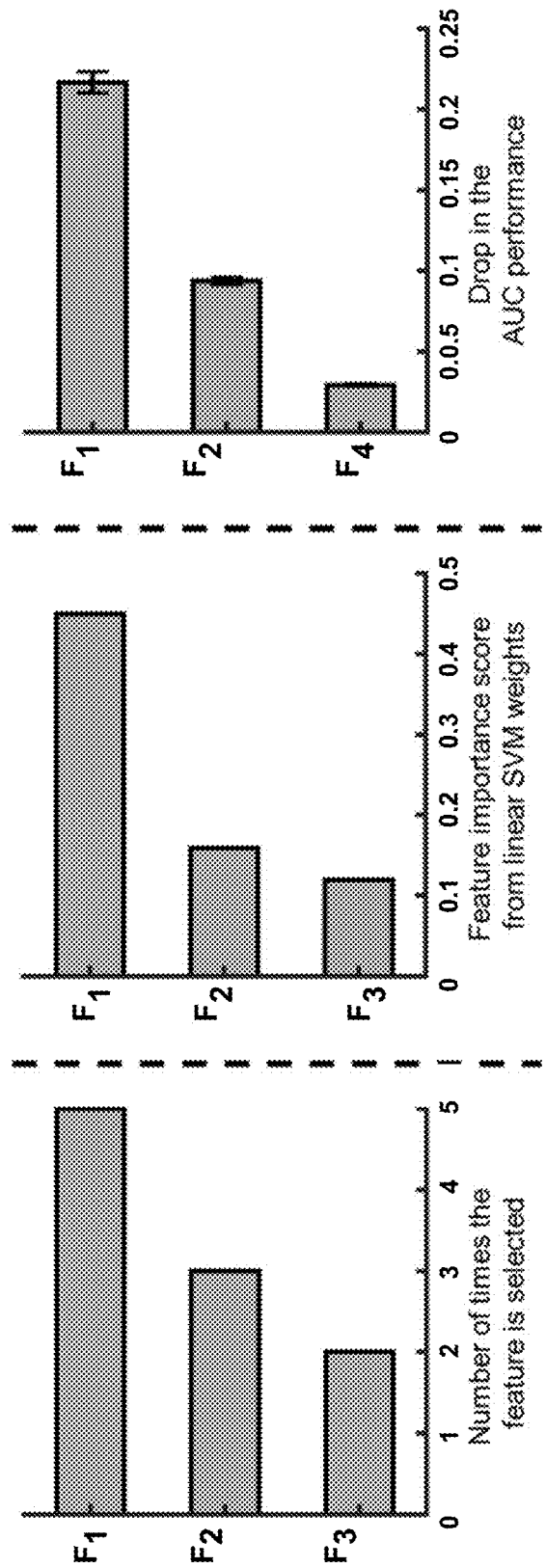
FIG. 16A provides a bar graph showing the number of times a feature is selected using SFS in performing five-fold cross validation, in accordance with the present disclosure.
FIG. 16B provides bar graph showing the features that have the top three importance scores computed using linear support vector machines (SVMs) feature weights, in accordance with the present disclosure.
FIG. 16C provides a bar graph showing the top three most important features as evaluated by the permutation feature importance method, in accordance with the present disclosure.

After processing a recording, a total of 83 features, including RR interval as a feature, were extracted. Using SFS, greedy feature selection was leveraged to determine a subset of features that are sub-optimized for performing the classification task. FIGS. 16A-C show the feature votes as an estimate of feature importance, as well as results from two additional approaches more commonly used in assessing feature importance. In FIG. 16A, the bar graph shows the number of times a feature is selected out of five cross-validation splits. The more the feature is selected, the more important it is. In FIG. 16B, feature importance is computed based on linear SVM's separating hyperplane weights. The higher the weight is, the more the decision is affected by changes in that specific feature, indicating importance of the feature. Lastly, permutation feature importance analysis is run where each one of the feature's values is shuffled and the resultant decrease in performance is observed. The higher the decrease in the performance by permutation, the more important is the feature. The results of permutation feature importance are shown in FIG. 16C. Notably, in all three feature importance analyses, the top two features remain the same. Both features are extracted from the lateral axis of the SCG, and the second feature is directly computed from the diastolic portion of the SCG beats.

Discussion

The results in FIGS. 14A-B and TABLE IX demonstrate that accurate classification of HF patients' clinical status is possible using SCG features. Currently, the determination of the clinical status of HF patients for physiological decompensation requires catheterization, which is expensive and invasive. If this wearable device can provide data that facilitates accurate classification of clinical status, it can be used as a pre-screening tool to reduce the number of RHC procedures, which can reduce HF care costs and improve quality of life. The results from this study suggest that such pre-screening with SCG holds promise.

The accurate classification of HF clinical status is significant as it demonstrates that elevated filling pressures can potentially be detected from patients with HF. Accurate classification of clinical status at home with a wearable device can greatly improve HF care through reduced hospitalizations. Daily or more frequent assessment of the clinical status with the wearable device can allow filling pressure guided therapy similarly to the approach used in prior work with implantable hemodynamic monitors. Importantly, by providing an indication of elevated filling pressure rather than a black box output driving a decision as in prior work, physicians can better engage with the process with explainable and interpretable results; moreover, existing flow charts and guidelines can be directly leveraged.

The features selected in the experiments along with the feature importance analyses provide important scientific insight into the characteristics of SCG signals (see FIGS. 16A-C). While SCG signals have been measured and studied since the 1960s, the origin of these signals and their relationship to underlying hemodynamic events is not well understood. This study directly measured SCG signals together with RHC waveforms in patients with HF, thus allowing the examination of how SCG characteristics (features) represent underlying hemodynamics. The optimal set of features selected by SFS of the best performing classifier were derived from Lat and magnitude channels, thus demonstrating the importance of analyzing all axes of SCG signal data rather than just DV, as suggested also by some prior work. The top two features were derived from the Lat channel of the SCG consistently across all the feature importance methods. The finding that the Lat channel of the SCG provides key hemodynamic information is also supported by recent work. The top feature stems from the frequency domain and has not been previously studied: the ratio of higher frequency components (205-250 Hz) to lower frequency components (4-50 Hz) is a discriminatory feature. This could be due to higher filling pressures in the decompensated patients. Higher filling pressures could lead to louder or more rapid valve closures which can reflect as higher frequency components of the acceleration signal captured on the chest. Future work should study the lateral SCG measurements to better understand the physiological origin of these vibrations to provide mechanistic insight into the reasons behind their important contribution to clinical status estimation.

This is the first study that demonstrated the utility of SCG signals in classifying HF clinical status in resting state and detecting elevated filling pressures. The results presented in this study set a strong scientific foundation for supporting the investigation of SCG signals in at-home settings for HF care with the potential to reduce HF related hospitalizations. Moreover, the work has the potential to deliver feedback to healthcare providers by not just predicting the risk of hospitalization (i.e., acute decompensation) but also providing an indication of elevated filling pressures.

Materials and Methods

A. Study Design

The aim of the study was to explore the discriminative features of SCG in differentiating the clinical status (i. e. decompensated and compensated states) of HF patients in a resting state and investigating the correlation between SCG and hemodynamic parameters. Data are collected from a cohort of patients for whom RHC (performed using Mac-Lab Hemodynamic Recording System) was prescribed to determine the clinical status and capture the hemodynamic parameters. The study was administered under a protocol reviewed and approved by the University of California, San Francisco (UCSF) Institutional Review Board and the Georgia Institute of Technology Institutional Review Board. A total of 63 subjects diagnosed with HF were enrolled in the study. Exclusion criteria were patients in cardiogenic shock, or with implanted ventricular assist devices or prior heart transplantation. Demographics of the study population are shown in TABLE VII (training set) and TABLE VIII (validation set). Each subject provided written informed consent before the data collection.

All the SCG data were collected while patients were undergoing the RHC procedure. The patient, firstly, rested supine on a procedure table. The wearable patch hardware was attached to just below the jugular notch of the patient to acquire SCG signals. During the procedure, the patient was instructed to remain as still as possible. Then, the catheter was inserted, and the hemodynamic parameters were measured. The supine position and the motionless state of the patient is referred to as the resting state. All the signals collected during a single RHC procedure are referred to as a recording, which consists of ECG and SCG signals from the wearable patch and pressure waveforms from the catheterization, which uses Mac-Lab Hemodynamic Recording System (total of 65 recordings). Moreover, compensated recording is defined as a recording acquired from a patient who is determined to be hemodynamically compensated and similarly for decompensated recording. The data collection setup, along with example signal excerpts, is illustrated in FIG. 1E.

Based on the RHC procedure, the following hemodynamic parameters were measured per recording: right atrial pressure (RAP), right ventricular pressure (RVP), PAP, cardiac output (CO), and PCWP. Based on the hemodynamic parameters, clinical status was determined as follows by clinicians: if a patient had a mean PCWP of 20 mmHg or more and a CI of 2.2 L/min/m$^2$ or less, the patient was considered decompensated. Otherwise, the patient was considered compensated. In some rare cases, this rule was overridden by the caregivers if one of the PCWP or CI values were unusually high/low. For example, a patient with borderline PCWP of 16 mmHg combined with extremely low CI of 1.3 L/min/m$^2$ was considered decompensated. Note that two patients underwent RHC procedure twice and thus the number of recordings is two more than the number of patients in the training set.

In this Example, a wearable patch device was used to capture SCG and ECG signals. The device samples the ECG signal at 1 kHz and the accelerometer signals at 500 Hz and saves the data into a micro secure digital (microSD) card in the patch. Custom software transfers all the data from the microSD card to a computer and resamples the accelerometer to 1 kHz such that all signals share the same sampling rate for ease of processing. All signals are then decimated to 500 Hz in our processing algorithms for further analysis.

SCG signals are processed to extract features that could be useful in discriminating the clinical status of HF patients. FIGS. 2A-C illustrates how the processing of SCG signals are carried out. As a result of the processing, we acquire high quality SCG beats, which can be seen in FIG. 2C, for feature extraction.

The first preprocessing step is to remove five minutes from the beginning and the end of each recording, since in some recordings the sensor starts recording before the device is attached to the subject and ends recording after device is detached. As a second step, the ECG signals were band-pass filtered with the following digital filter specifications: FIR filter with pass band of 1-30 Hz. For SCG signals, the signal was high-pass filtered with a cutoff frequency of 1 Hz. In both filters, stopbands are attenuated by 80 dB. The pass band for the ECG signal was chosen as to isolate the R-peaks for easier detection of them in the next processing step. For the SCG signal, the pass band was chosen to suppress out-of-band noise and preserve the SCG signal characteristics and to explore high-frequency components.

After filtering both the ECG and SCG signals, two additional channels of SCG were formed that are referred to as the magnitude channel and XY magnitude channel, represented by the equations below:

$$SCG_{Mag}[n] = \sqrt{SCG_x[n]^2 + SCG_y[n]^2 + SCG_z[n]^2} \quad \text{Equation 3:}$$

$$SCG_{XYMag}[n] = \sqrt{SCG_x[n]^2 + SCG_y[n]^2} \quad \text{Equation 4:}$$

where $SCG_x[n]$, $SCG_y[n]$ and $SCG_z[n]$ are the Lat, HtoF and DV channels of SCG, respectively.

As a final pre-processing step, R-peaks in the ECG signal were detected and subsequently beat segmentation in SCG signals was performed. For R-peak detection, two algorithms were used: Pan-Tompkins, implemented by Physionet; and the Phasor Transform, with a custom implementation. R-peaks that were detected from both algorithms were selected to reduce false positives in R-peak detection. For detection, 12 second windows were used to detect the R-peaks.

Using the R-peaks, beat segmentation of SCG signal was carried out in the following way: 150 ms before the R-peak (to include ventricular diastole) and 15th percentile of RR intervals after the R-peak (to include only the current beat) was delimited as the start and end of a beat, respectively. As a result, SCG beat arrays were constructed for each channel of SCG. Note that in contrast to prior works that perform beat segmentation from the R-peak (i.e., 0 ms before/after the R-peak) to approximately 700 ms after the R-peak, in this example, ventricular diastolic timing was deliberately included since it was expected that the SCG features observed during this time may be quite relevant for including information about filling pressures.

B. Motion Artifact Rejection and SQI

SCG signals are susceptible to motion artifacts: when a subject moves, SCG vibrations are contaminated by higher amplitude motion artifacts. In the collected dataset, even though patients were instructed to remain as still as possible, motion artifacts were still present in recordings. FIGS. 3A-D illustrate examples of such artifacts in one recording.

By leveraging the observation that motion artifacts are of higher amplitude than SCG vibrations, we devised a simple algorithm to detect motion-corrupted SCG beats and subsequently discard motion-contaminated SCG beats. This algorithm inputs the segmented beat array and outputs the indices of motion-contaminated beats. The pseudo-code is shown in Algorithm 1 (above). The key to the detection is the search for two consecutive beats that are the most similar. If the two consecutive beats are not contaminated by motion, they should be similar in morphology because in a short period of time we do not expect a substantial change in SCG morphology. The most similar two consecutive beats, therefore, should be free of motion artifacts (see FIG. 3C for an example of the most similar two consecutive beats in this recording). By computing a simple threshold using the motion artifact free part of the recording, we detect the motion artifacts as outlined in Algorithm 1 (above). The result of the motion artifact detection algorithm is illustrated in FIGS. 3A-D.

To measure the similarity between two beats, the following formula was used:

$$\text{Similarity}(\vec{b_1}, \vec{b_2}) = 1 - \frac{\left\| \frac{\vec{b_1}}{\|\vec{b_1}\|_\infty} - \frac{\vec{b_2}}{\|\vec{b_2}\|_\infty} \right\|_2}{2\sqrt{M}} \quad \text{Equation 5}$$

where $\vec{b_1}, \vec{b_1} \in R^M$. The range of values that the output of this formula can yield is between 0 and 1. If the output is closer to 1, the inputs are more similar and if the output is closer to 0, inputs are more dissimilar.

Aftermotion artifact contaminated beats are detected and rejected, SQI, was applied separately to each channel of SCG to extract high quality SCG beats. One approach can result in a family of templates being extracted from a set of subjects and then used to analyze SCG recordings from subsequent subjects. While this approach attempts to generalize across subjects, it was found to yield unsatisfactory templates in this application. It is hypothesized that the use of healthy subjects in a prior work made it relatively straightforward to extract a generalizable set of templates, while in this case the HF population exhibits significantly greater heterogeneity. The solution is to use a specific set of templates from each recording (i.e., from each patient). Specifically, one template per each channel of SCG for a subject. With these changes, the template is tailored for the specific subject and without any motion artifact. The output of SQI is a set of beats with a quality score associated with each beat. The top 5% of the beats was used based on the quality measure to extract the features.

C. Statistical Analyses

Standard analyses were used to evaluate the classification quality of clinical status estimation models. The ground truth data is collected from catheter measurements. Specifically, five-fold cross validation was performed on a training set and estimated performance on separate unseen validation set.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. An apparatus, comprising:
   a set of electrodes configured to measure an electrocardiogram signal of a heart of a user, the set of electrodes attachable to a chest of the user; and
   a wearable device configured to be worn on the chest of the user below a suprasternal notch of the user, the wearable device including:
   a housing having a first side and a second side, the first side configured to face away from the chest and the second side configured to face toward the chest when the wearable device is attached to the set of electrodes;
   a set of connectors disposed on the second side of the housing in spaced relation to one another, each connector of the set of connectors configured to releasably attach to a different electrode of the set of electrodes;
   an accelerometer disposed within an interior of the housing between the first side and the second side, the accelerometer configured to measure a set of seismocardiogram signals of the user, each seismocardiogram signal of the set of seismocardiogram signals being a channel associated with a different axis of a set of axes; and electronics operatively coupled to the set of electrodes and the accelerometer, the electronics including a processor and a memory, the processor configured to execute instructions stored in the memory to:

receive the electrocardiogram signal and the set of seismocardiogram signals of the user;

segment the set of seismocardiogram signals based on the electrocardiogram signal to construct seismocardiogram beat arrays for the set of axes, each seismocardiogram beat array including a plurality of seismocardiogram signal segments associated with a plurality of beats;

input the seismocardiogram beat arrays into a motion-artifact detection algorithm that compares morphologies of seismocardiogram signal segments of consecutive beats of the plurality of beats to compute similarity values of those seismocardiogram signal segments to identify one or more seismocardiogram signal segments that are dissimilar based on the similarity values and outputs indices of motion-contaminated beats, the comparing of the morphologies of the seismocardiogram signal segments of consecutive beats by the motion-artifact detection algorithm configured to identify motion artifacts having amplitudes higher than underlying local mechanical vibrations of the chest of the user associated with a movement of blood within vasculature of the user;

remove, from the seismocardiogram beat arrays, the motion-contaminated beats;

apply signal quality indexing to each seismocardiogram signal of the set of seismocardiogram signals using as a template an ensemble average of the seismocardiogram signal segments of the plurality of beats after removing the motion-contaminated beats to extract high quality beats from the plurality of beats, each of the high quality beats having a quality score in a top predetermined percentage of the plurality of beats;

extract, using a machine learning algorithm, features from the seismocardiogram signal segments of the high quality beats;

determine one or more hemodynamic parameters associated with filling characteristics of the heart using the extracted features; and output, via a display, the one or more hemodynamic parameters.

2. The apparatus of claim 1, wherein the processor is further configured to execute instructions stored in the memory to:

determine one or more hemodynamic parameters associated with at least one of pulmonary artery pressure or pulmonary capillary wedge pressure of the heart using the extracted features.

3. The apparatus of claim 1, wherein the set of axes includes a lateral axis, a head-to-foot axis, and a dorsoventral axis.

4. The apparatus of claim 1, wherein the processor is further configured to execute instructions stored in the memory to:

generate an assessment of heart health of the user based on the one or more hemodynamic parameters, wherein the heart health of the user is associated with heart failure.

5. The apparatus of claim 1, wherein the processor is further configured to execute instructions stored in the memory to:

detect R-peaks in the electrocardiogram signal, and the processor is configured to segment the set of seismocardiogram signals based on the R-peaks.

6. The apparatus of claim 5, wherein detecting the R-peaks in the electrocardiogram signal includes implementing at least one of Pan Tompkins or a Phasor Transform to process the electrocardiogram signal to detect the R-peaks.

7. The apparatus of claim 5, wherein the processor is further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

8. The apparatus of claim 1, wherein the one or more hemodynamic parameters includes a filling pressure of the user or a change in the filling pressure of the user.

9. An apparatus, comprising:

a set of electrodes configured to measure an electrocardiogram signal of a heart of a user, the set of electrodes attachable to a chest of the user; and a wearable device configured to be worn on the chest of the user below a suprasternal notch of the user, the wearable device including:

a housing having a first side and a second side, the first side configured to face away from the chest and the second side configured to face toward the chest when the wearable device is attached to the set of electrodes; and a set of connectors disposed on the second side of the housing in spaced relation to one another, each connector of the set of connectors configured to releasably attach to a different electrode of the set of electrodes;

an accelerometer disposed within an interior of the housing between the first side and the second side, the accelerometer configured to measure a set of seismocardiogram signals of the user, each seismocardiogram signal of the set of seismocardiogram signals being a channel associated with a different axis of a set of axes; and electronics operatively coupled to the set of electrodes and the accelerometer, the electronics including a processor and a memory, the processor configured to execute instructions stored in the memory to:

receive the electrocardiogram signal and the set of seismocardiogram signals of the user;

segment the set of seismocardiogram signals based on the electrocardiogram signal to construct seismocardiogram beat arrays for the set of axes, each seismocardiogram beat array including a plurality of seismocardiogram signal segments associated with a plurality of beats;

implement a motion-artifact detection algorithm that:

compares, for each axis of the set of axes, morphologies of seismocardiogram signal segments of consecutive beats of the plurality of beats to compute similarity values of those seismocardiogram signal segments for each axis;

determines combined similarity values for those seismocardiogram signal segments based on the similarity values for each axis;

rejects one or more seismocardiogram signal segments that are dissimilar based on the combined similarity values; and outputs the seismocardiogram beat arrays without the one or more seismocardiogram signal segments that are dissimilar, the one or more seismocardiogram signal segments that are dissimilar having motion artifacts with amplitudes higher than underlying local mechanical vibrations of the chest of the user associated with a movement of blood within vasculature of the user;

apply signal quality indexing to each seismocardiogram signal of the set of seismocardiogram signals using as a template an ensemble average of the seismocardiogram signal segments of the plurality of beats without the one or more seismocardiogram signal segments that are dissimilar to extract high quality beats from the plurality of beats, each of the high quality beats having a quality score in a top predetermined percentage of the plurality of beats;

extract, using a machine learning algorithm, features from the seismocardiogram signal segments of the high quality beats;

determine one or more hemodynamic parameters associated with filling characteristics of the heart using the extracted features; and output, via a display, the one or more hemodynamic parameters.

10. The apparatus of claim 9, wherein the processor is further configured to execute instructions stored in the memory to:

prior to segmenting the set of seismocardiogram signals, apply one or more cut-off frequencies to the set of seismocardiogram signals to remove out-of-band noise associated with the set of seismocardiogram signals.

11. The apparatus of claim 9, wherein the set of axes includes a lateral axis, a head-to-foot axis, or a dorso-ventral axis.

12. The apparatus of claim 9, wherein the processor is further configured to execute instructions stored in the memory to:

detect R-peaks in the electrocardiogram signal, and the processor is configured to segment the set of seismocardiogram signals based on the R-peaks.

13. The apparatus of claim 12, wherein detecting the R-peaks in the electrocardiogram signal includes implementing at least one of Pan Tompkins or a Phasor Transform to process the electrocardiogram signal to detect the R-peaks.

14. The apparatus of claim 12, wherein the processor is further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

15. The apparatus of claim 9, wherein the one or more hemodynamic parameters includes a filling pressure of the user or a change in the filling pressure of the user.

16. An apparatus, comprising:

a set of electrodes configured to measure an electrocardiogram signal of a heart of a user, the set of electrodes attachable to a chest of the user; and a wearable device configured to be worn on the chest of the user below a suprasternal notch of the user, the wearable device including:

a housing having a first side and a second side, the first side configured to face away from the chest and the second side configured to face toward the chest when the wearable device is attached to the set of electrodes; and a set of connectors disposed on the second side of the housing in spaced relation to one another, each connector of the set of connectors configured to releasably attach to a different electrode of the set of electrodes;

an accelerometer disposed within an interior of the housing between the first side and the second side, the accelerometer configured to measure a set of seismocardiogram signals of the user, each seismocardiogram signal of the set of seismocardiogram signals being a channel associated with a different axis of a set of axes; and electronics operatively coupled to the electrodes and the accelerometer, the electronics including a processor and a memory, the processor configured to execute instructions stored in the memory to:

receive the electrocardiogram signal and the set of seismocardiogram signals of the user;

segment the set of seismocardiogram signals based on the electrocardiogram signal to construct seismocardiogram beat arrays for the set of axes, each seismocardiogram beat array including a plurality of seismocardiogram signal segments associated with a plurality of beats;

input the seismocardiogram beat arrays into a motion-artifact detection algorithm that compares morphologies of seismocardiogram signal segments of consecutive beats of the plurality of beats to compute similarity values of those seismocardiogram signal segments to identify one or more seismocardiogram signal segments that are dissimilar based on the similarity values and output indices of motion-contaminated beats, the comparing of the morphologies of the seismocardiogram signal segments of consecutive beats by the motion-artifact detection algorithm configured to identify motion artifacts having amplitudes higher than underlying local mechanical vibrations of the chest of the user associated with a movement of blood within vasculature of the user:

remove, from the seismocardiogram beat arrays, the motion-contaminated beats;

apply signal quality indexing to each seismocardiogram signal of the set of seismocardiogram signals using as a template an ensemble average of the seismocardiogram signal segments of the plurality of beats after removing the motion-contaminated beats to extract high quality beats from the plurality of beats, each of the high quality beats having a quality score in a top predetermined percentage of the plurality of beats;

determine one or more hemodynamic parameters associated with filling characteristics of the heart based on the seismocardiogram signal segments of the high quality beats; and output, via a display, the one or more hemodynamic parameters.

17. The apparatus of claim 16, wherein the processor is further configured to execute instructions stored in the memory to:

determine one or more hemodynamic parameters associated with at least one of pulmonary artery pressure or pulmonary capillary wedge pressure of the heart based on the seismocardiogram beat arrays after removing the motion-contaminated beats.

18. The apparatus of claim 16, wherein the set of axes includes a lateral axis, a head-to-foot axis, and a dorso-ventral axis.

19. The apparatus of claim 16, wherein the processor is further configured to execute instructions stored in the memory to:

generate an assessment of heart health of the user based on the one or more hemodynamic parameters, wherein the heart health of the user is associated with heart failure.

20. The apparatus of claim 16, wherein the processor is further configured to execute detect R-peaks in the electrocardiogram signal, and the processor is configured to segment the set of seismocardiogram signals based on the R-peaks.

21. The apparatus of claim 20, wherein detecting the R-peaks in the electrocardiogram signal includes implementing at least one of Pan Tompkins or a Phasor Transform to process the electrocardiogram signal to detect the R-peaks.

22. The apparatus of claim 20, wherein the processor is further configured to segment the set of seismocardiogram signals by delimiting, for each beat of the plurality of beats, a first predetermined time before an associated R-peak of the R-peaks as a start of the beat and a second predetermined time after the associated R-peak of the R-peaks as an end of the beat, such that the start and the end of the beat captures ventricular diastolic timing.

23. The apparatus of claim 22, wherein the one or more hemodynamic parameters includes a filling pressure of the user or a change in the filling pressure of the user.

* * * * *

UNITED STATES PATENT AND TRADEMARK OFFICE
CERTIFICATE OF CORRECTION

| | | |
|---|---|---|
| PATENT NO. | : 12,336,793 B1 | Page 1 of 1 |
| APPLICATION NO. | : 18/751868 | |
| DATED | : June 24, 2025 | |
| INVENTOR(S) | : Omer T. Inan et al. | |

It is certified that error appears in the above-identified patent and that said Letters Patent is hereby corrected as shown below:

On the Title Page

Item (72) Inventors, Line 1 delete "Varol" and insert --Varon--

Signed and Sealed this
Twelfth Day of August, 2025

Coke Morgan Stewart
*Acting Director of the United States Patent and Trademark Office*